United States Patent
Gilbert et al.

(10) Patent No.: US 7,094,345 B2
(45) Date of Patent: Aug. 22, 2006

(54) IMPLEMENTATION OF MICROFLUIDIC COMPONENTS, INCLUDING MOLECULAR FRACTIONATION DEVICES, IN A MICROFLUIDIC SYSTEM

(75) Inventors: John R. Gilbert, Brookline, MA (US); Manish Deshpande, Canton, MA (US); Jaishree Trikha, Waban, MA (US)

(73) Assignee: Cytonome, Inc., Watertown, MA (US)

( * ) Notice: Subject to any disclaimer, the term of this patent is extended or adjusted under 35 U.S.C. 154(b) by 0 days.

(21) Appl. No.: 10/816,514

(22) Filed: Mar. 31, 2004

(65) Prior Publication Data
US 2004/0245102 A1     Dec. 9, 2004

Related U.S. Application Data

(63) Continuation-in-part of application No. 10/329,018, filed on Dec. 23, 2002, now Pat. No. 6,878,271.

(60) Provisional application No. 60/459,028, filed on Mar. 31, 2003, provisional application No. 60/501,734, filed on Sep. 9, 2003, provisional application No. 60/410,685, filed on Sep. 13, 2002, provisional application No. 60/409,489, filed on Sep. 9, 2002.

(51) Int. Cl.
*B01D 63/00*    (2006.01)
*B01L 11/00*    (2006.01)
*B01D 57/00*    (2006.01)

(52) U.S. Cl. ............... 210/321.61; 210/321.75; 210/321.84; 422/101; 422/104; 204/450; 977/DIG. 1

(58) Field of Classification Search ............... 210/632, 210/635, 321.6, 85; 204/450; 422/101, 422/104; 977/DIG. 1
See application file for complete search history.

(56) References Cited

U.S. PATENT DOCUMENTS

| | | | |
|---|---|---|---|
| 5,216,126 A | 6/1993 | Cox et al. | |
| 5,498,392 A * | 3/1996 | Wilding et al. ............ 422/68.1 |
| 5,565,365 A | 10/1996 | Glass | |
| 5,770,029 A | 6/1998 | Nelson et al. | |
| 5,922,210 A | 7/1999 | Brody et al. | |
| 5,922,591 A | 7/1999 | Anderson et al. | |
| 5,948,227 A | 9/1999 | Dubrow | |
| 5,948,441 A | 9/1999 | Lenk et al. | |
| 5,962,081 A | 10/1999 | Ohman et al. | |
| 5,993,661 A | 11/1999 | Ruckenstein et al. | |
| 6,007,775 A | 12/1999 | Yager | |
| 6,042,709 A | 3/2000 | Parce et al. | |
| 6,046,056 A | 4/2000 | Parce et al. | |
| 6,051,380 A | 4/2000 | Sosnowski et al. | |
| 6,139,831 A | 10/2000 | Shivashankar et al. | |
| 6,156,527 A | 12/2000 | Schmidt et al. | |
| 6,168,948 B1 | 1/2001 | Anderson et al. | |
| 6,187,190 B1 | 2/2001 | Smith et al. | |
| 6,197,595 B1 | 3/2001 | Anderson et al. | |
| 6,197,599 B1 | 3/2001 | Chin et al. | |
| 6,221,600 B1 | 4/2001 | MacLeod et al. | |

(Continued)

OTHER PUBLICATIONS

Adam, et al. "Chemical strategies for functional proteomics." *Mol Cell Proteomics*. Oct. 2002; 1(10):781-90.

(Continued)

*Primary Examiner*—W. L. Walker
*Assistant Examiner*—Krishnan S Menon
(74) *Attorney, Agent, or Firm*—Lahive & Cockfield, LLP

(57) ABSTRACT

A system and method for integrating microfluidic components in a microfluidic system enables the microfluidic system to perform a selected microfluidic function. A capping module includes a microfluidic element for performing a microfluidic function. The capping module is stacked on a microfluidic substrate having microfluidic plumbing to incorporate the microfluidic function into the system. The microfluidic element may comprise a matrix having an affinity for selected molecules in a sample. The matrix binds, reacts with and/or retains the selected molecules without affecting other molecules in the sample.

22 Claims, 29 Drawing Sheets

U.S. PATENT DOCUMENTS

| | | | |
|---|---|---|---|
| 6,306,590 | B1 | 10/2001 | Mehta et al. |
| 6,306,628 | B1 | 10/2001 | Rothschild et al. |
| 6,316,266 | B1 | 11/2001 | Nelson |
| 6,429,025 | B1 | 8/2002 | Parce et al. |
| 6,432,290 | B1 | 8/2002 | Harrison et al. |
| 6,440,725 | B1 | 8/2002 | Pourahmadi et al. |
| 6,444,461 | B1 | 9/2002 | Knapp et al. |
| 6,482,607 | B1 | 11/2002 | Reymond et al. |
| 6,488,897 | B1 | 12/2002 | Dubrow et al. |
| 6,498,039 | B1 | 12/2002 | Nelson |
| 6,531,283 | B1 | 3/2003 | Kingsmore et al. |
| 2001/0041357 | A1 | 11/2001 | Fouillet et al. |
| 2002/0015952 | A1* | 2/2002 | Anderson et al. ............... 435/6 |
| 2002/0106786 | A1 | 8/2002 | Carvalho et al. |
| 2003/0027354 | A1* | 2/2003 | Geli ........................... 436/178 |
| 2003/0215941 | A1* | 11/2003 | Campbell et al. ........... 435/325 |

OTHER PUBLICATIONS

Adam, et al. "Proteomic profiling of mechanistically distinct enzyme classes using a common chemotype." *Nat Biotechnol.* Aug. 2002; 20(8):805-9.

Blagoev, et al., "A Proteomics strategy to elucidate functional protein-protein interactions applied to EGF signaling." *Nat Biotechnol.* Mar. 2003; 21(3):315-8.

Fey, et al. "2D or not 2D. Two-dimensional gel electrophoresis." *Curr Opin Chem Biol.* Feb. 2001; 5(1):26-33.

Gao, et al. "Integrated microfluidic system enabling protein digestion, peptide separation, and protein identification." *Anal. Chem.* 2001, 73:2648-55.

Gorg, et al. "The current state of two-dimensional electrophoresis with immobilized pH gradients." *Electrophoresis.* Apr. 2000; 21(6):1037-53.

Graves, et al. "Molecular biologist's guide to proteomics." *Microbiol Mol Biol Rev.* Mar. 2002; 66(1):39-63.

Gygi, et al. "Evaluation of two-dimensional gel electrophoresis-based proteome analysis technology." *Proc Natl Acad Sci USA.* Aug. 15, 2000; 97(17):9390-5.

Jessani, et al. "Enzyme activity profiles of the secreted and membrane proteome that depict cancer cell invasiveness." *Proc Natl Acad Sci USA.* Aug. 6, 2002; 99(16):10335-40.

Jiang, et al. "Integrated plastic microfluidic devices with esi-ms for drug screening and residue analysis." *Anal. Chem.* 2001, 73:2048-53.

Joberty, et al., "Borg proteins control septin organization and are negatively regulated by Cdc42." *Nat Cell Biol.* Oct. 2001; 3(10):861-6.

Kidd, et al. "Profiling serine hydrolase activities in complex proteomes." *Biochemistry.* Apr. 3, 2001; 40(13):4005-15.

Lilley, et al. "Two-dimensional gel electrophoresis: recent advances in sample preparation, detection and quantitation." *Curr Opin Chem Biol.* Feb. 2002; 6(1):46-50.

Mann, et al. "Analysis of proteins and proteomes by mass spectrometry." *Annu Rev Biochem.* 2001; 70:437-73.

Mann, et al. "Proteomic analysis of post-translational modifications." *Nat Biotechnol.* Mar. 2003; 21(3):255-61.

Oda, et al. "Enrichment analysis of phosphorylated proteins as a tool for probing the phosphoproteome." *Nat Biotechnol.* Apr. 2001; 19(4):379-82.

Ong, et al. "An evaluation of the use of two-dimensional gel electrophoresis in proteomics." *Biomol Eng.* Nov. 2001; 18(5):195-205.

Pandey, et al. "Analysis of receptor signaling pathways by mass spectrometry: identification of vav-2 as a substrate of the epidermal and platelet-derived growth factor receptors." *Proc Natl Acad Sci USA.* Jan. 4, 2000; 97(1):179-84.

Sydor, et al. "Protein expression profiling arrays: tools for the multiplexed high-throughput analysis of proteins." *Proteome Sci.* Jun. 10, 2003; 1(1):3.

Wang, et al. "Integration of polymeric membranes with microfluidic networks for bioanalytical applications." *Electrophoresis.* 2001; 22:3857-67.

Wang, et al. "High resolution chiral separation using microfludics-based membrane chromatography." *Journal of Chromatography A 942.* 2002; 115-22.

Xiang, et al. "An integrated microfabricated device for dual microdialysis and on-line ESI-ion trap mass spectrometry for analysis of complex biological samples." *Anal. Chem.* 1999; 71:1485-90.

Xu, et al. "A microfabricated dialysis device for sample cleanup in electrospray ionization mass spectrometry." *Anal. Chem.* 1998; 70:3553-6.

\* cited by examiner

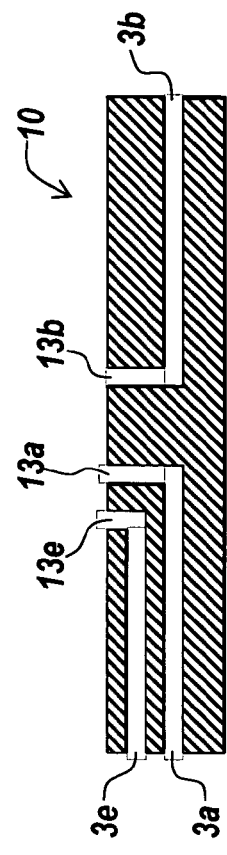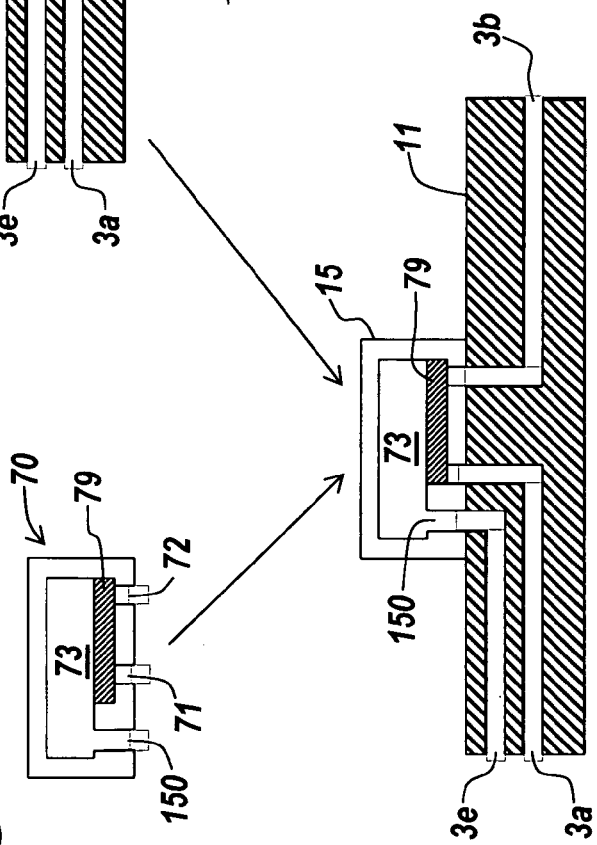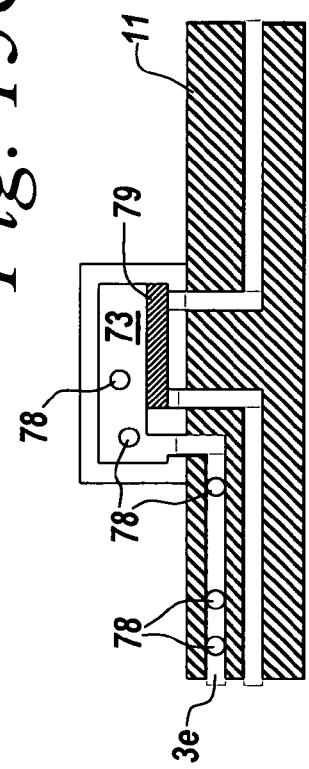

IMPLEMENTATION OF MICROFLUIDIC COMPONENTS, INCLUDING MOLECULAR FRACTIONATION DEVICES, IN A MICROFLUIDIC SYSTEM

RELATED APPLICATIONS

The present application is a continuation-in-part of U.S. patent application Ser. No. 10/329,018, filed Dec. 23, 2002, now U.S. Pat. No. 6,878,271 entitled "Implementation of Microfluidic Components in a Microfluidic System" and claims priority to U.S. Provisional Patent Application Ser. No. 60/459,028, filed Mar. 31, 2003, entitled "Molecular Fractionation Devices" and U.S. Provisional Patent Application Ser. No. 60/501,734, filed Sep. 9, 2003, entitled "Molecular Fractionation Devices", the contents of which are herein incorporated by reference.

FIELD OF THE INVENTION

The present invention relates to a microfluidic system for handling fluid samples on a microfluidic level. More particularly, the present invention relates to a microfluidic system for separating or filtering particles, such as cells, in a suspension.

BACKGROUND OF THE INVENTION

Microfluidic devices and systems provide improved methods of performing chemical, biochemical and biological analysis and synthesis: Microfluidic devices and systems allow for the performance of multi-step, multi-species chemical operations in chip-based micro chemical analysis systems. Chip-based microfluidic systems generally comprise conventional 'microfluidic' elements, particularly capable of handling and analyzing chemical and biological specimens. Typically, the term microfluidic in the art refers to systems or devices having a network of processing nodes, chambers and reservoirs connected by channels, in which the channels have typical cross-sectional dimensions in the range between about 1.0 μm and about 500 μm. In the art, channels having these cross-sectional dimensions are referred to as 'microchannels'.

In the chemical, biomedical, bioscience and pharmaceutical industries, it has become increasingly desirable to perform large numbers of chemical operations, such as reactions, separations and subsequent detection steps, in a highly parallel fashion. The high throughput synthesis, screening and analysis of (bio)chemical compounds, enables the economic discovery of new drugs and drug candidates, and the implementation of sophisticated medical diagnostic equipment. Of key importance for the improvement of the chemical operations required in these applications are an increased speed, enhanced reproducibility, decreased consumption of expensive samples and reagents, and the reduction of waste materials.

In the fields of biotechnology, and especially cytology and drug screening, there is a need for high throughput filtration of particles. Examples of particles that require filtration are various types of cells, such as blood platelets, white blood cells, tumorous cells, embryonic cells and the like. These particles are especially of interest in the field of cytology. Other particles are (macro) molecular species such as proteins, enzymes and poly-nucleotides. This family of particles is of particular interest in the field of drug screening during the development of new drugs.

Proteomics is one of the main areas of modern biology, and has recently gained significant importance in biology, primarily because proteins are involved in virtually every cellular function, control every regulatory mechanism and are modified in disease (as a cause or effect). The proteome consists of all proteins present in a complex sample at a given time, including proteins translated directly from genetic material and a variety of modified proteins. These modified proteins can arise from alternative splicing of transcripts, or by extensive post-translation modifications (such as glycosylation, amidation, ubiquitination, phosphorylation, methylation) or by a combination of the two resulting in modifications that alter the function and/or structure of the protein. An aspect of proteomics often called "protein expression profiling" involves the qualitative and quantitative study of protein expression in samples that differ by some variable. Protein expression profiling has been used to find markers for disease states, to understand signaling networks in cells, and to look for new targets for drug design. The combination of high resolution separations and mass spectrometry (MS) analysis of peptide fragments have resulted in great ability to take a sample (from tissue, cells, serum, or subcellular fraction) and identify many, or all, of the proteins present, and gain an understanding of their state and abundance.

Available state-of-the-art analytical methodologies for protein expression profiling require extensive sample preparation and have complex sample handling requirements. Current technologies are also limited in their ability to recognize alterations in functional and structural properties of proteins (e.g. various states of post-translational modification). Therefore, there is an urgent need to develop a new class of analytical methodologies that can provide accurate, sensitive and more detailed information than available in current approaches.

Two common approaches exist to make use of MS identification of peptides in protein profiling. In one type of protein profiling (known as "digest-before-separate"), one takes the protein sample and digests the mixture down to peptide fragments, followed by liquid chromatography (LC) separation of the fragments and MS—MS analysis of the fragment sequence. In the other type (known as "separate-before-digest"), a protein mixture is separated by high resolution 2D Electrophoresis (2DE) (currently immobilized pH gradient (IPG) isoelectric focusing followed by SDS-PAGE) and then protein spots on the final 2D gel are excised, digested, and deposited on a surface for MALDI-MS analysis.

Experiments that use the "separate-before-digest" techniques for protein profiling generally fall into two classes. In the first class, called "global" protein profiling, a mixture of proteins is thrown at the 2DE system or a set of 2DE systems (each with a different narrow IPG) with a goal of resolving the entire proteome of the sample (or as much as was able to load on the 2DE system) and detecting, excising, digesting, and identifying the interesting spots with MALDI-MS. While this approach is simple and powerful and (when running multiple narrow range 2D gels on the same sample) has been reported to resolve more than 10000 proteins from a higher eukaryotic cell lysate, the global approach has the weakness that no little or no functional information is revealed by the separation itself and high abundance proteins are known to mask low abundance proteins. Additionally, the need for extremely high resolution in global methods requires the use of 2DE separation which has some known difficulties in its own right in the areas of: handling low abundance proteins (because overloading causes loss of resolution and high abundance proteins can mask low abundance spots); extreme pI proteins (less than 3 and more than 9); cysteine rich proteins (which often smear under isoelectric focusing); and a general difficulty in reproducing 2DE patterns from lab to lab.

An alternative to the "global" approach is a "fractionated" protein profiling approach, which generally involves using affinity columns, bead precipitation and/or selective labeling to fractionate the initial protein sample into one or more sub-proteomes. The sub-proteomes are then separated, digested and identified as in the global approach. Advantages of the "fractionated" approach include the fact that a protein is a member of the selected fraction can be very revealing as to its function or its state.

An example of the fractionated protein profiling approach is Post-Translational Modification (PTM). Several groups have isolated proteins phosphorylated on either tyrosine or serine/threonine residues. By construction, all bands in these experiments have undergone some post translational modification, and in sample difference experiments a band appearing or disappearing directly indicates phosphorylation modulated signaling in those samples.

Another example of fractionated protein profiling is Activity-Based Protein Profiling (ABPP). By employing probes that covalently link to an enzyme active site fractions of "active" enzyme families have been isolated for separation.

Yet another example of fractionated protein profiling is Protein—Protein interaction. By binding "bait" proteins to beads and isolating the fraction of proteins that bind to the bait many groups have studied protein—protein interactions.

A final example is Sub-Proteome Elution. Using an elution column of heparin-sepharose whole cell proteomes of CHO and RCC cells can be fractionated into 3 sub-proteomes.

In the fractionated approach, the problem of identifying the proteins in a sub-proteome is reduced by reducing the number of proteins that are separated from thousands of proteins to less than about a hundred proteins (depending on how stringent the fractionation is). This both allows increased loading of the proteins that remain in the fraction (relative to the amount of those proteins that would be loadable if part of an unfractionated mixture) and removes a large quantity of possibly masking proteins. In many cases the separation problem is reduced enough to be tractable with one-dimensional electrophoresis (1DE) instead of 2D, which allows one to take advantage of the superiority of 1DE, including greater loading capacity, better ability to handle large protein complexes (above 100 kDa), better ability to handle extreme pI and hydrophobic proteins, better quantitation, and generally more reliability and consistency from run-to-run. In some cases enough information is gleaned from the labeling and fractionation to make it unnecessary to go to MS.

A "fractionated" approach to protein expression analysis then has some real advantages in terms of information content, reliability, sensitivity and spectrum of proteins that can be handled. However, the fractionated approaches to protein expression analysis require a manual affinity purification step before a separation procedure, which is not very well defined or automatable. Current fractionated approaches therefore are slow, with, at best, procedure of a least on day in duration to go from gel to MALDI-MS.

SUMMARY OF THE INVENTION

The present invention provides a system and method for integrating microfluidic components in a microfluidic system to enable the microfluidic system to perform a selected microfluidic function. The present invention utilizes a capping module including a microfluidic element for performing a microfluidic function. The capping module is stacked on a microfluidic substrate having microfluidic plumbing to incorporate the microfluidic function into the system.

According to one aspect, a molecular fractionation device is incorporated into a microfluidic system using a capping structure having a matrix provided therein for segregating biomolecules according to their physical and biological properties. The molecular fractionation device of the present invention may be used to selectively capture macromolecules from one flow stream for later release into another flow stream. The molecular fractionation device of the present invention may also be used to process macromolecules from one flow stream with matrix bound reactants or enzymes. The molecular fractionation device of the present invention may also be used to form a molecular detector by binding signal generating reagents or enzymes to the fixed matrix.

In one embodiment, the molecular fractionation device comprises a matrix enclosed and stored in a capping module, so that the molecular fractionation device can later be assembled onto an underlying chip having plumbing formed therein. The molecular fractionation device may also be assembled onto the chip having plumbing formed therein without a matrix, and the matrix may be inserted into the molecular fractionation device by flow from the chip. Alternatively, a matrix is pre-loaded into the molecular fractionation device and subsequently modified in situ to be fully functional or "programmed".

The molecular fractionation device may be used in a variety of applications. For example, the device may be used for sample fractionation in which fractions are extracted from a mixture of proteins based on each fraction having affinity for the matrix in a corresponding molecular fractionation device, and where a plurality of molecular fractionation devices are arranged in series to extract fractions from a single sample.

In another application, a molecular fractionation device of may capture a sample fraction and subsequently elute sub-fractions of the sample fraction from the molecular fractionation device by flowing a step gradient or a continuous gradient of concentrations of a buffer that reduces the affinity of that fraction to that molecular fractionation device.

In another application, a two-dimensional separation technique employs a plurality of molecular fractionation devices to fractionate a plurality of proteins. Subsequently, each fraction is eluted off of the corresponding molecular fractionation device with a continuous or step gradient in the concentration of an eluent. In the two-dimensional separation technique, one dimension corresponds to the type of affinity matrix in the series of molecular fractionation devices, and the other dimension corresponds to the quantitative binding affinity of each protein to the matrix of the molecular fractionation device.

A molecular fractionation device of the invention may also be used for three-dimensional protein separation, in which a sample of proteins is fractionated by a molecular fractionation device, and then eluted in steps to make bands of different affinity. Each band is then injected into an open or gel-filled capillary electrophoresis (CE) column to be separated on the basis of size or charge or charge/mass ratio.

A plurality of molecular fractionation device may be implemented in a multidimensional programmable affinity fractionation system for protein identification, extraction, elution and dispensing. Such a system incorporates a set of technologies that can separate proteins using biochemical molecular criteria in addition to physical properties such as molecular weight and isoelectric focusing. Affinity fractionation provides an additional dimension that provides the ability to distinguish between molecules whose amino acid sequences are identical but which differ in expression levels and post-translational modifications and hence functionality.

Any of the described applications of the molecular fractionation device of the present invention may be combined with microfluidic ejectors to enable separated protein bands to be ejected or removed from a chip to multiwell plates or microarray slides. The ejection of the protein bands enables further processing and/or analysis in the multiwell plates or further analysis and/or MALDI-Mass Spectrometry using the microarray slides.

Any of the applications described above may be followed with an on-chip process that digests the separated proteins with a reactive-molecular fractionation device containing trypsin. Microfluidic ejection components may then be used to enable separated protein bands to be ejected or removed from chip to microarray slides. This would be of particular utility when using the slides as an input to MALDI-MS.

According to a first aspect of the invention, a microfluidic system is provided, which comprises a first microchannel formed in a substrate, a first communication port coupling the first microchannel to a surface of the substrate and a capping module having a matrix having an affinity for selected molecules and a trapping filter for compartmentalizing the matrix on the capping module. The capping module is adapted to be stacked on the substrate and placed in communication with the first microchannel.

In another aspect of the invention, a capping module for a microfluidic system comprises a substrate, a matrix disposed on the substrate having an affinity for selected molecules, and a trapping filter for compartmentalizing the matrix on the substrate.

According to another aspect of the invention, a molecular fractionation device for a microfluidic system is provided, which comprises a capping module comprising a substrate defining a region for holding a matrix, a trapping filter for compartmentalizing a matrix on the substrate and a connector port for placing the region for holding a matrix in fluid communication with an exterior of the substrate, wherein the trapping filter covers the connector port.

In yet another aspect of the invention, a method for segregating molecules based on a selected property comprises the steps of providing a first molecular fractionation device including a matrix for binding molecules having the selected property, flowing a sample containing molecules having the selected property through the matrix, such that molecules having the selected property are retained by the matrix, and passing molecules not having the selected property through a first outlet of the molecular fractionation device.

According to still another aspect of the invention, a method of processing a sample, comprises the steps of providing a molecular fractionation device including a matrix having enzymes that react with selected fractions of the sample, and passing a buffer containing the sample through the molecular fractionation device, whereby the enzymes react with and process the selected fractions of the sample to form a reacted sample.

According to yet another aspect of the invention, a method of analyzing a sample, comprises the steps of passing the sample through a molecular fractionation device including a matrix including detection molecules that react with the sample to produce a measurable reaction and detecting the measurable reaction.

According to another aspect, a method of fabricating a molecular fractionation device, comprises the steps of providing a capping module and bonding a trapping filter to the capping module to form a chamber for holding a matrix.

In still another aspect of the invention, a microfluidic system comprises a first channel for conveying a sample and a plurality of molecular fractionation devices coupled to the channel and arranged in series. A first outlet of a first molecular fractionation device is in communication with a first inlet of a second molecular fractionation device, and each molecular fractionation device includes a matrix having an affinity for a selected set of molecules.

According to still another aspect of the invention, a method for protein expression profiling comprises the steps of fractionating a protein into a plurality of fractions using a plurality of molecular fractionation devices, wherein each molecular fractionation device includes a matrix having an affinity for one of said fractions, and eluting each of said plurality of fractions from the molecular fractionation devices as bands of different affinities.

According to a final aspect of the invention, a molecular fractionation device comprises a capping module having a chamber for holding a matrix having an affinity for selected molecules, a trapping filter for compartmentalizing the matrix in the chamber, a first connector port for placing the chamber in communication with a first microchannel, a second connector port for placing the chamber in communication with a second microchannel, a third connector port for placing the chamber in communication with a third microchannel, and a fourth connector port for placing the chamber in communication with a fourth microchannel.

BRIEF DESCRIPTION OF THE FIGURES

FIGS. 15A–15D illustrate a manufacturing process for a molecular fractionation device, wherein the device is built and stored without a matrix, and the matrix is subsequently added to the device after assembly with a chip.

DETAILED DESCRIPTION OF THE INVENTION

Figure 1:
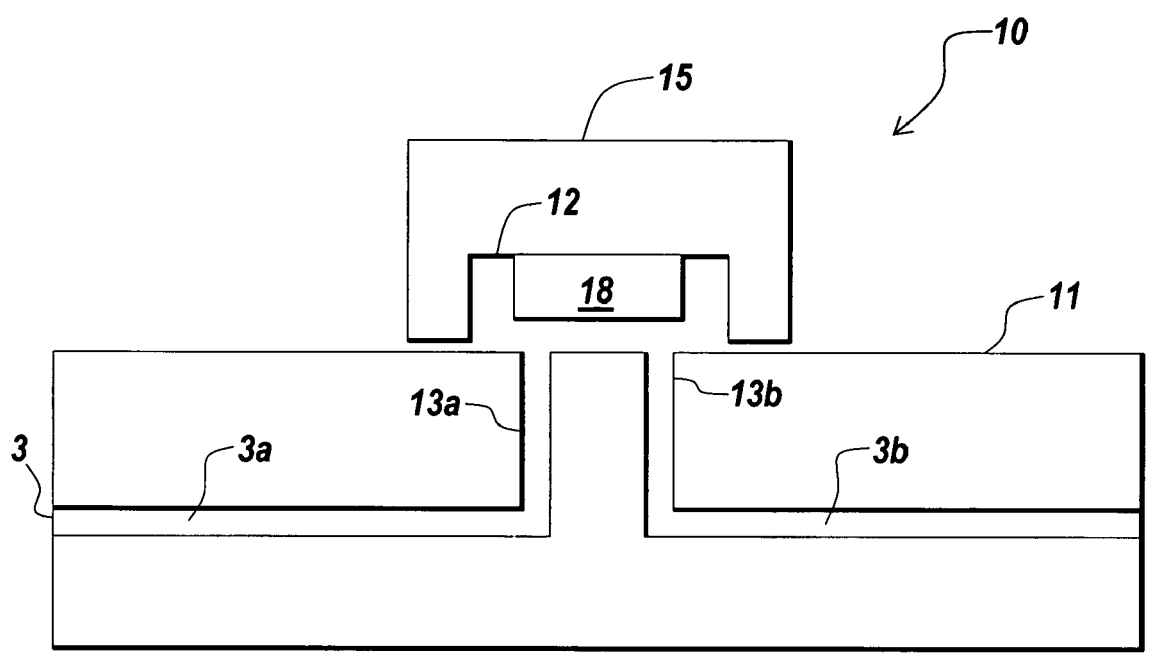
FIG. 1 illustrates a microfluidic system including a capping structure for integrating a microfluidic function into the microfluidic system.

The present invention provides a microfluidic component comprising a capping module including a microfluidic element for performing a microfluidic function. The capping module is stacked on a microfluidic substrate having microfluidic plumbing to incorporate the microfluidic function into the system. In one embodiment, the invention comprises a molecular fractionation device for allowing on-chip fractionation of a sample. The present invention will be described below relative to an illustrative embodiment. Those skilled in the art will appreciate that the present invention may be implemented in a number of different applications and embodiments and is not specifically limited in its application to the particular embodiments depicted herein.

As used herein, the term "microfluidic" refers to a system or device for handling, processing, ejecting and/or analyzing a fluid sample including at least one channel having microscale dimensions.

The terms "channel" and "flow channel" as used herein refers to a pathway formed in or through a medium that allows for movement of fluids, such as liquids and gases. The channel in the microfluidic system preferably have cross-sectional dimensions in the range between about 1.0 μm and about 500 μm, preferably between about 25 μm and about 250 μm and most preferably between about 50 μm and about 150 μm. One of ordinary skill in the art will be able to determine an appropriate volume and length of the flow channel. The ranges are intended to include the above-recited values as upper or lower limits. The flow channel can have any selected shape or arrangement, examples of which include a linear or non-linear configuration and a U-shaped configuration.

The term "port" refers to a structure for providing fluid communication between two elements.

The term "substrate" as used herein refers to a support structure having channels formed therein for conveying a fluid.

The terms "cap" or "capping module" as used herein refer to a structure, which is the same size as or smaller than a substrate, having any selected size or shape and formed of any selected material, and having a microfluidic element. The capping module is configured to stack on or communicate with the substrate to fully or partially complete a fluid path, or to be disposed in contact with or adjacent thereto.

The term "microfluidic element" as used herein refers to a component in a microfluidic system for performing a microfluidic function, including, but not limited to: beads, passive check valves, active valves, pressure sensors, connecting channels, membrane filtration units, threaded taps for external connecting tubes, compression chambers, pumps, and others that may be known to those of ordinary skill in the art.

The term "microfluidic function" as used herein refers to any operation, function or process performed or expressed on a fluid or sample in a microfluidic system, including, but not limited to: filtration, dialysis, pumping, fluid flow regulation, controlling fluid flow and the like.

As used herein the term "matrix" refers to a solid support with appropriate chemistry having an affinity for selected molecules. A matrix according to the present invention may be used to bind, retain and/or react with desired biomolecules. An example of a suitable matrix includes, but is not limited to, affinity beads having any chemistry, including, but not limited to antibodies, small and large molecule ligands, molecular "baits" and transport molecules, such as albumin.

The term "membrane" or "filter" as used herein refers to a material of any suitable composition and size, which may used to separate or filter substances by size exclusion or other measures.

As used herein, the term "molecular fractionation device" refers to a device for segregating biomolecules according to their physical and biological properties.

As used herein, the term "affinity column" refers to a molecular fractionation device comprising beads with specialized chemistry for separating or reacting with biomolecules.

The term "substance" as used herein refers to any material used in a microfluidic process, including, but not limited to chemical compounds, molecules, viruses, cells, particles, beads, buffers, or any other material used in a microfluidic process.

The term "protein" refers to a polypeptide or a molecule made up of polypeptides.

The term "reagent" as used herein refers to a buffer solution with inorganic and organic salts.

The term "sample" as used herein refers to a solution containing a biological molecule.

The term "enzyme" as used herein refers to a biological molecule that reacts with another molecule.

As used herein, "pump" refers to a device suitable for intaking and discharging fluids and can have different sizes, including microscale dimensions, herein referred to as "micropump."

An illustrative embodiment of the present invention provides a microfluidic system and method for rapidly segregating biomolecules according to their physical and biological properties. The microfluidic system of the invention is applicable to proteomic, genomic and other solutions. The system utilizes biochemical, physical, structural and chemical properties of biomolecules for multidimensional molecular separation. The illustrative system captures biomolecules directly from a crude preparation, followed by selective elution by varying chemical composition of the buffer. Biomolecule separation may be achieved by using beads with specialized chemistry, which are selected based on the biochemical properties of the biomolecule of interest. By coupling capillary electrophoresis with affinity elution, the peak resolution ca) be increased significantly.

The present invention allows implementation of different microfluidic functions into a microfluidic chip using a microfluidic component comprising a capping module having a microfluidic element for performing a microfluidic function. As shown in FIG. 1, a microfluidic chip 10 suitable for implementing an embodiment of the invention comprises a substrate 11 having one or more flow channels 3, illustrated as a microchannel, disposed therein. The flow channels transport fluid through the microfluidic system 10 for processing, handling, and/or performing any suitable operation on a liquid sample. The microfluidic system 10 may comprise any suitable number of flow channels 3 for transporting fluids through the microfluidic system 10.

As shown in FIG. 1, the flow channel 3 is formed in a substrate 11, and may connect to the surface of the substrate via one or more communication ports 13a and 13b. A microfluidic component 12 is provided for performing a microfluidic function on a sample. The microfluidic component 12 comprises a capping module 15 including a microfluidic element 18, such as a filter, one or more valves, pressure sensors or other component for performing a microfluidic function, is placed over the substrate 11 to form a closed fluid path. According to an alternate embodiment, the capping module may include a connector channel for re-routing fluid flow through the microchannel around another structure. The illustrative substrate 11 includes two communication ports 13a, 13b, each connecting unconnected segments 3a, 3b of the flow channel 3 to the substrate surface, though one skilled in the art will recognize that variations may be made in the size, number and configuration of the communication ports and flow channels.

The illustrative capping module 15 may include connector ports for interfacing with the communication ports of the substrate, and/or a chamber 12, channel or recess to provide a fluidic path between the first connector port and the second connector port. One skilled in the art will recognize that the capping module may have alternate configurations and is not limited to the embodiment shown in FIG. 1.

Using the capping module 15, microfluidic functions, such as filtration, dialysis, pumping, flow control and so on, may be integrated into the microfluidic system 10 without requiring significant modification of the substrate 11. A substrate including any number and arrangement of conduits or channels 3 for conveying fluids can be transformed into a functional fluidic circuit by selecting and placing one or more capping modules 15 with a functional microfluidic element 18 on the substrate, i.e chip. According to an illustrative embodiment, the same automated "pick and place" surface mount equipment technology used to make integrated circuits may be used to form fluidic circuits on a substrate having microchannels using various capping structures. Suitable pick and place equipment is manufactured by Manncorp, Inc. (Huntingdon Valley, Pa.), among others.

To fabricate a fluidic circuit, the channels 3 in the substrate 11 may be manufactured by chip microfabrication. The channels or plumbing may be fabricated by etching half-channels in a first substrate, followed by bonding and/or lamination of a second substrate to enclose the half-channels, forming a microchannel. The substrate may be formed of one or more layers containing etched channels if more complex fluidic networks are required. The communication ports may then be fabricated in the substrate to connect the microchannel to an exterior surface of the substrate. Suitable techniques for fabricating the communication ports include drilling, laser etching, powder blasting or other techniques known in the art. After the fabrication of the substrate and communication ports, a capping module having a desired functionality is bonded to the substrate to form a microfluidic component in the larger microfluidic circuit.

A variety of capping module number and sizes may be bonded to the substrate to form a variety of microfluidic components for imparting various microfluidic functions to form a microfluidic system. The capping modules may be removable and replaceable so that a substrate may be re-used.

According to the illustrative embodiment, the capping module has a cross-sectional dimension of between about 1 millimeter and about 5 centimeters, though those skilled in the art will recognize that the invention is not limited to this range. The capping module may be formed of any suitable material, including, but not limited to plastic, glass, silicon and other materials known in the art.

The microfluidic chip 10 may include one or more microfluidic components, alone or in combination, configured to facilitate processing of a sample. For example, the microfluidic component may comprise a microfiltration system for separating substances in solution, such as separating selected particles from cells or other particles in a suspension. The microfluidic component may comprise an aliquoting, mixing and incubation component, such as an on-chip sample dilution system, for processing a sample, such as performing a mixture of a specific amount of sample and reagent. The microfluidic component may also form a valve for selectively controlling the flow of fluid through the channels, a pump for pumping fluid through the channels or a molecular fractionation device for fractionating samples. One skilled in the art will recognize that variations in the configuration, position, number and combination of the various microfluidic components may be made in accordance with the present invention.

Figure 2:
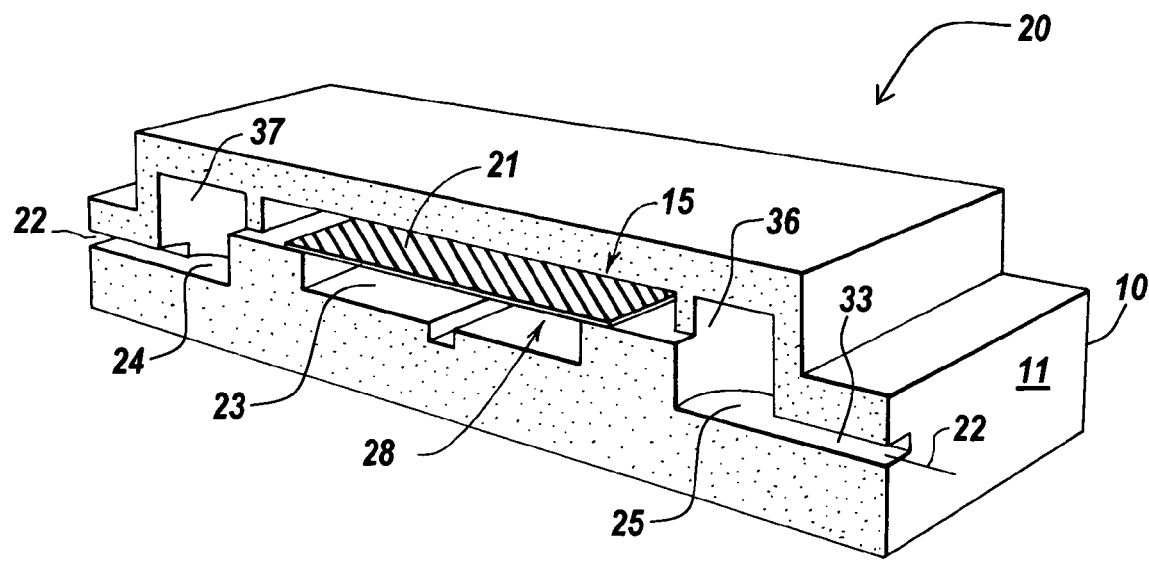
FIG. 2 is a perspective, cross-sectional view of a microfiltration system formed according to an illustrative embodiment of the invention.

For example, the capping module may integrate conventional membrane filter technology into a microfluidic chip to create a filtration system 20, shown in FIG. 2. The filtration system can be inserted into an existing microfluidic chip to enable filtration of particles, cells or other substances in suspension without requiring significant or expensive modification of the chip structure.

Figure 3:
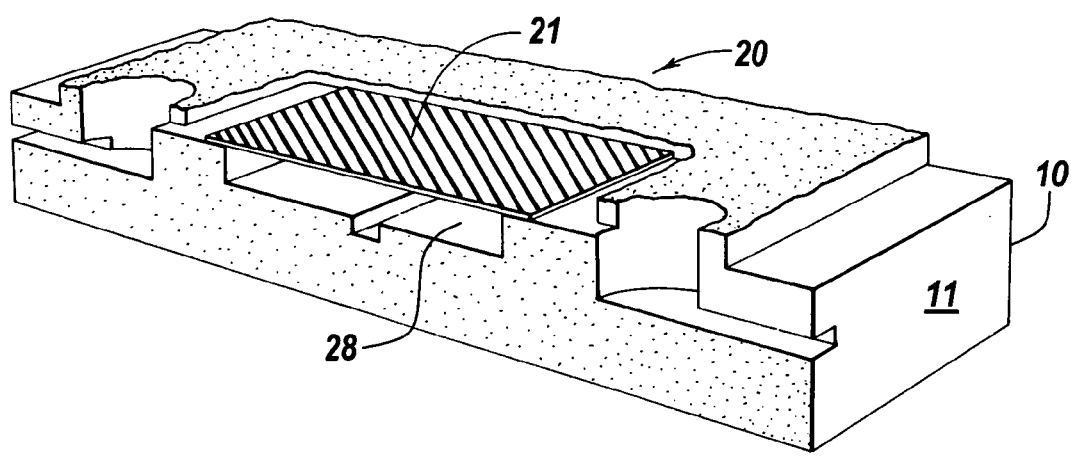
FIG. 3 is a detailed view of the membrane on the microfiltration system of FIG. 2.
Figure 4:
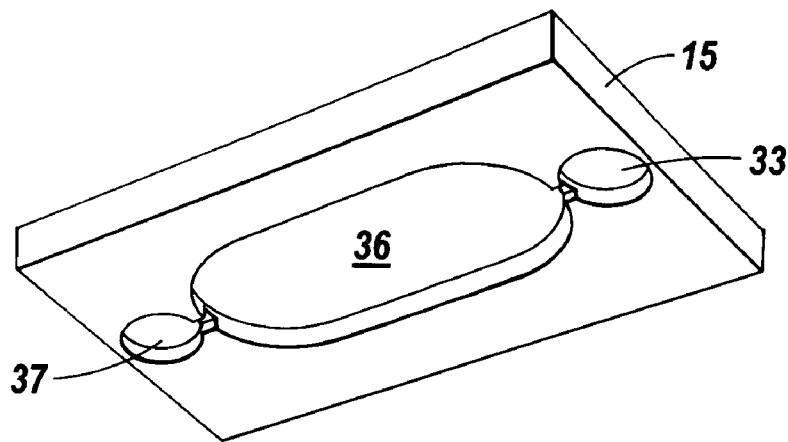
FIG. 4 illustrates the microfabricated cap of the microfiltration system of FIG. 2.
Figure 5:
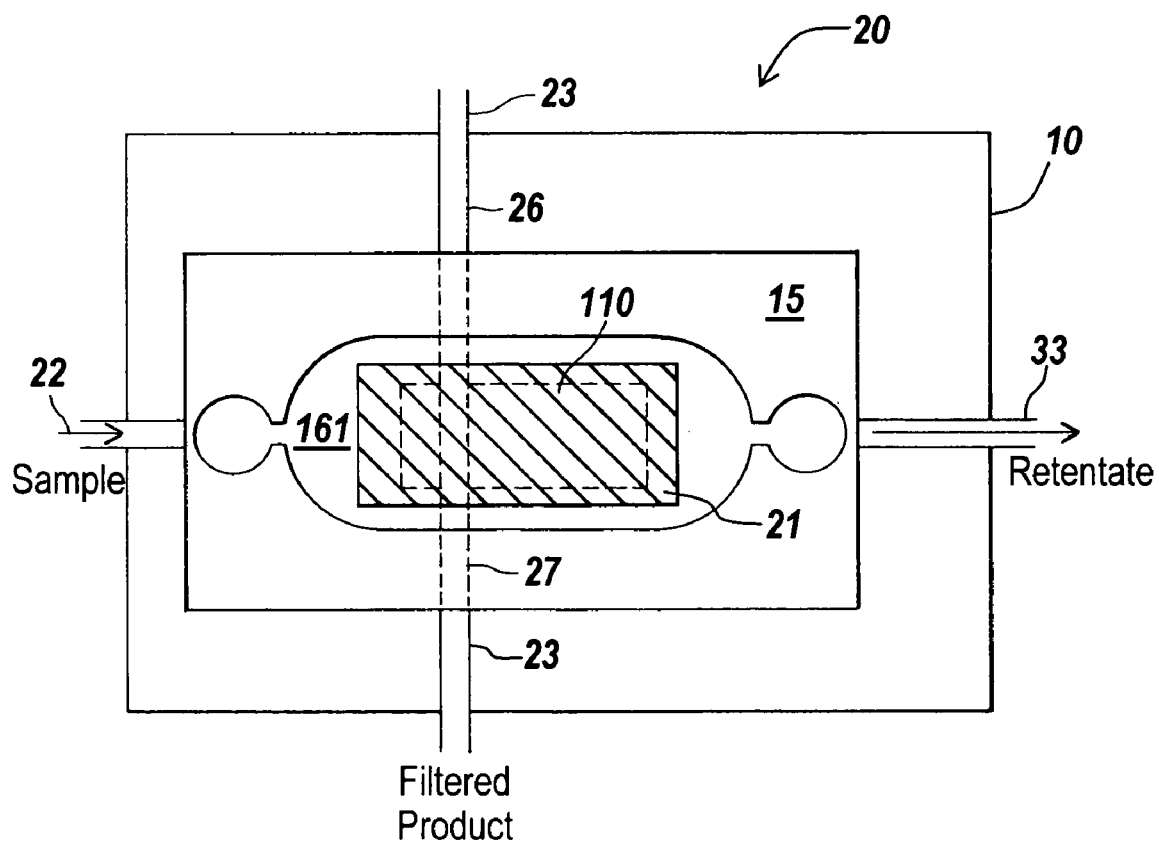
FIG. 5 is a top view of the microfiltration system of FIG. 2.

FIGS. 2, 3 and 5 illustrate a microfabricated filtration subsystem 20 suitable for implementation in the microfluidic system of FIG. 1 according to one embodiment of the invention. FIG. 4 illustrates an embodiment of the capping module 15 used to fabricate the filtration system 20 according to one embodiment of the invention. The illustrative filtration subsystem separates a substance, such as a sample comprising a mixture of particles and fluid, using a membrane 21, and subsequently collects the separated components. The filtration system may be used to separate blood cells from plasma, viruses from cells, beads from cells, chemical compounds, molecules or other substances that a membrane may be used to separate. As shown the filtration subsystem 20 is formed directly on the microfluidic chip 10 to add filtration capability to the chip without requiring significant modification or expense.

The filtration subsystem 20 utilizes a conventional membrane filter 21 separating two flow paths in the substrate 11 to provide small volume controllable filtration of a sample. The illustrative filtration system is a four-port transverse filter, which includes a first fluid flow path 22 for supplying a substance to the filtration system, such as a mixture of particles and fluid, and a second fluid flow path 23 for receiving and conveying a filtered product (i.e., a filtrate) from the filtration system. The first fluid flow path 22 includes a first communication port, illustrated as a first inlet channel 24 that intersects the filtration system at a first inlet 37. The first fluid flow path 22 includes a second communication port, illustrated as a first outlet channel 25 including an outlet 33 from the filtration chamber for receiving and conveying a retentate of the substance from the filtration system. The second fluid flow path includes an inlet channel 26 intersecting a filtrate chamber, which is defined by a recess below the membrane 21, at a second inlet and a second outlet channel 27 for transferring the filtered product from the filtration system. The second fluid flow path 23 may include a carrier fluid for conveying the filtered product. A flow source drives the flow of the mixture through the filtration system to effect separation of the components through the membrane. The flow source may comprise an off-chip syringe pump, a microfabricated peristaltic pump, a microfabricated syringe, or any suitable flow source known in the art, such as those described in U.S. Provisional Patent Application Ser. No. 60/391,868 entitled "Microfluidic System and Components", the contents of which are herein incorporated by reference.

The illustrative microfabricated filtration system 20 has a relatively small footprint (less than about one $mm^2$), resulting in a compact structure, low cost and relatively simple fabrication. The particle separator further provides relatively low strain rates with reduced or no blockage. The amount of fluid retained can be significant, if desired, and the design is scalable and repeatable for additional parsing steps, if desired.

The filtration subsystem of the present invention may be formed by providing a microfluidic chip including an intersection of the two flow channels 22, 23. The assembly process integrates simple batch fabricated components, and is relatively simple and low cost at high volume. According to an illustrative embodiment, the chip forms a recess 28 in communication with the second flow channel 23 at the intersection of the flow channels. The first flow channel 22 is initially separated from and divided by the recess 28. A suitable membrane 21 is affixed to the microfluidic chip, using an appropriate adhesive or other suitable fastening mechanism, to cover the recess, thereby defining a reservoir below the membrane for receiving the filtered product and transmitting the filter product through the second flow channel 23. The membrane may comprise any suitable filtering membrane known in the art.

The illustrative microfabricated capping module 15, shown in FIG. 4, is affixed above the membrane 21 to define a filtration chamber 36 at the intersection in communication with the first flow channel 22. The cap 15 may be affixed using an appropriate adhesive or other suitable fastening mechanism. The illustrative capping module 15 includes an inlet 37 and an outlet 33 in communication with the filtration chamber to connect the first flow channel 22 with the filtration chamber 36 and enable flow of a composition to be filtered through the filtration chamber over the membrane. Alternatively, the membrane 21 is affixed directly to the capping module 15 and the capping module is affixed to the substrate to integrate the filtration system onto the substrate. One skilled in the art will recognize that the capping module is not limited to the illustrative embodiment and that variations may be made in accordance with the teachings of the invention.

The composition to be filtered is introduced to the filtration subsystem from the inlet channel and passes into the filtration chamber and over the membrane 21. The components of the substance are fractionated by the membrane 21, with the smaller components, such as plasma, passing through the membrane, into the reservoir defined by the recess 28 and through the second flow channel 23. The remaining portion, such as blood cells, passes through the filtration chamber to the outlet of the first flow channel 22.

According to the illustrative embodiment, the substrate of the microfluidic chip may be formed of glass, plastic, silicon, quartz, ceramics or any other suitable material. In a microfluidic chip manufactured from glass, the chip may comprise two layers: the chip and the cap affixed to the chip to define the filtration subsystem. In a microfluidic chip formed of plastic, the components may be stamped into the plastic substrate.

Figure 6A:
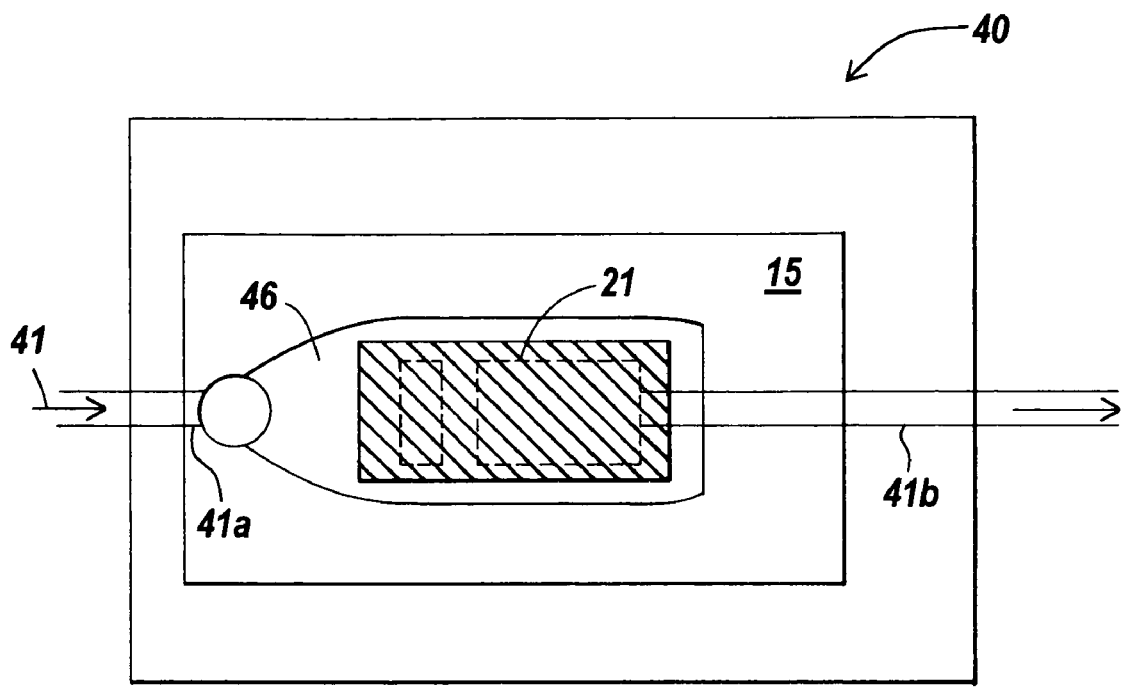
FIG. 6A is a top view of a two-port direct microfiltration system according to an alternate embodiment of the invention.
Figure 6B:
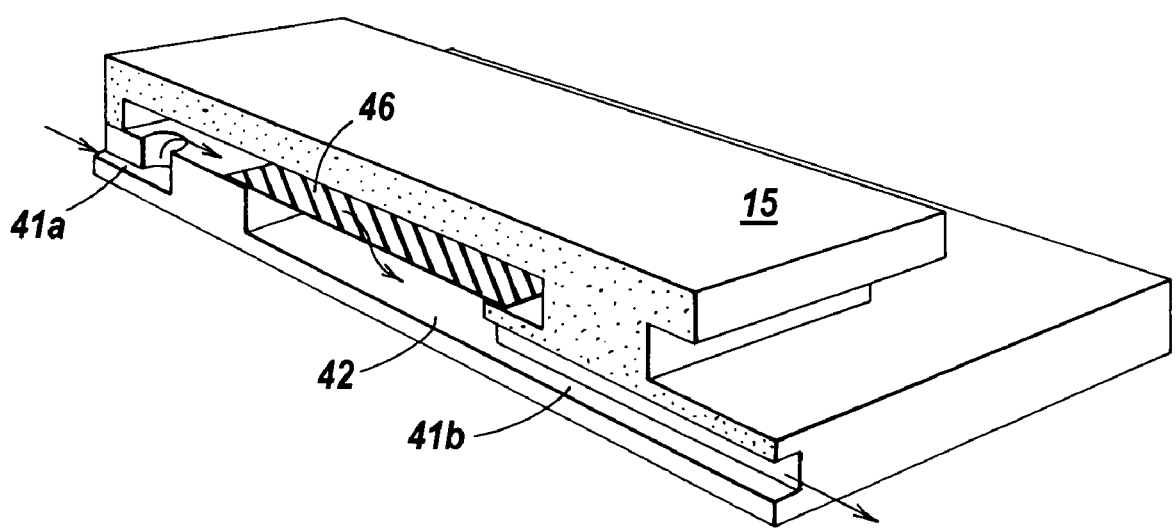
FIG. 6B is a perspective cross-sectional view of the microfiltration system of FIG. 6A.

According to an alternate embodiment, shown in FIGS. 6a and 6b, the microfiltration subsystem may comprise a two-port direct filter 40 comprising a membrane 21 inserted into a fluid flow path 41. As shown, the two-port direct filter 40 comprises a fluid flow path 41 formed in a microfluidic substrate, which is divided into two sections 41a, 41b. The second section 41b defines a recess 42 and the membrane 21 is adhered over the recess to define a filtrate chamber for receiving a filtered product. A microfabricated cap 15 including a recess 46 defining a filtration chamber is attached to substrate above the membrane to connect the flow path 41. The substance to be filtered is conveyed through the fluid flow path 41 into the filtration chamber 46 and passes through the membrane 21. The membrane 21 separates the substance by trapping larger molecules and the filtered product, comprising the remaining molecules, passes through the membrane along the fluid flow path 41 into the recess 42 and out of the microfiltration system for further analysis, processing collection, etc.

Figure 7A:
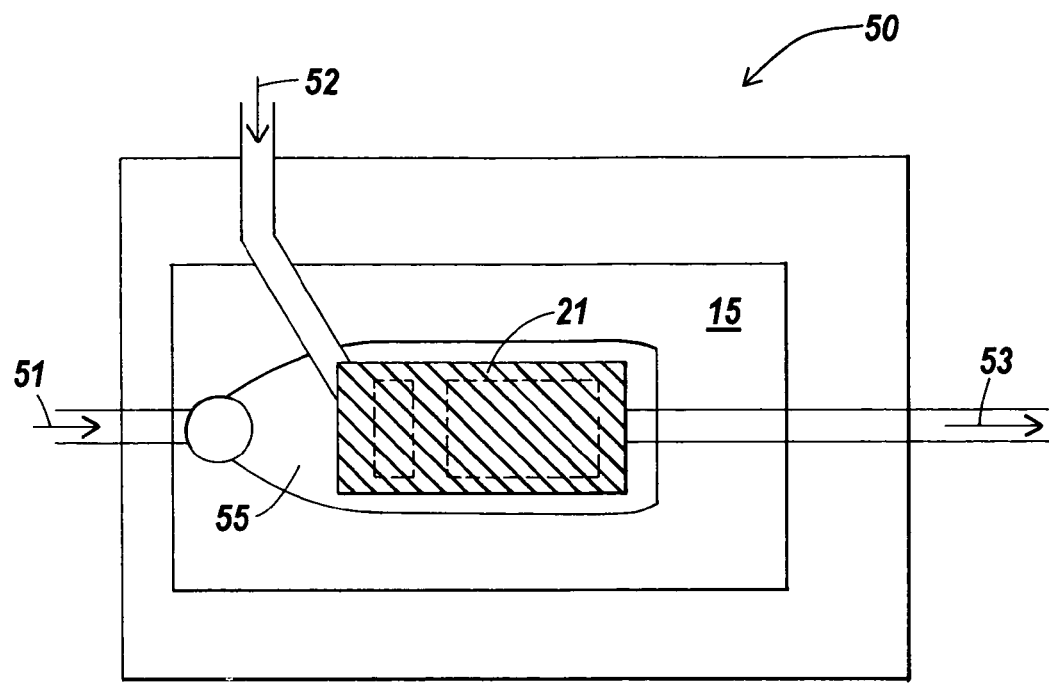
FIG. 7A is a top view of a three-port direct microfiltration system according to an alternate embodiment of the invention.
Figure 7B:
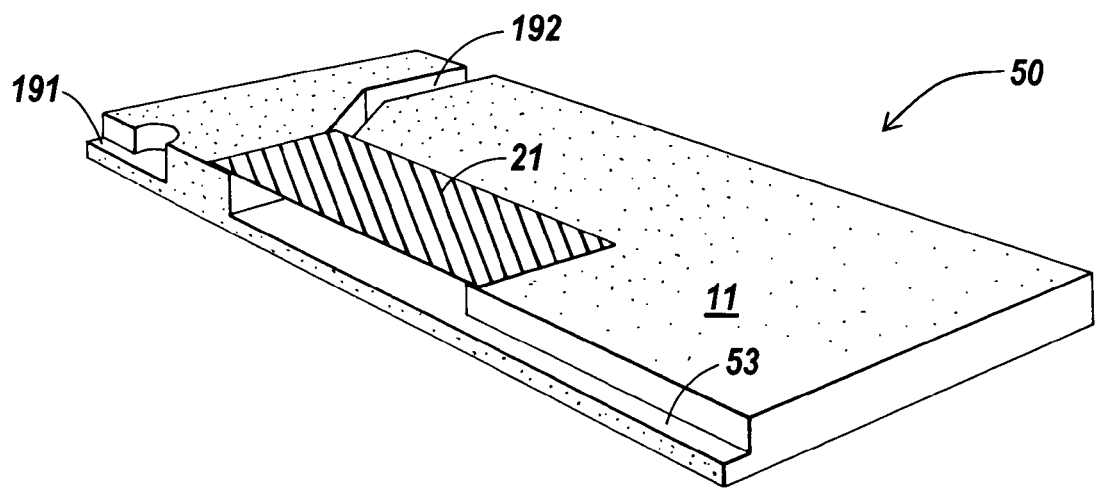
FIG. 7B is a perspective cross-sectional view of the microfiltration system of FIG. 7A, with the microfabricated cap removed.

According to yet another embodiment, shown in FIGS. 7a and 7b, the microfiltration system may comprise a three port direct filter 50. The three port direct filter 50 includes two inlet flow channels 51, 52 for inputting two samples to a filtration chamber 55 and a single outlet channel 53 for conveying a filtered product from the filter 50. The three-port direct filter includes a microfabricated cap 15 defining the filtration chamber and a membrane 21 separating the filtration chamber from the outlet channel 53. In operation, two samples may be provided through the inlet channels 51, 52. The samples mix together in the filtration chamber 55 and the sample mixture is filtered through the membrane, which separates the components of the sample mixture. The filtered product that passes through the membrane is conveyed through the outlet channel for further processing, analysis, collection etc.

One skilled in the art of membrane based separations will recognize that the filtration system described here can be used to implement on-chip separations of all types for which membranes may be found, including separating molecules by size or beads from molecules or small particles from large particles or viruses from cells or other separations known to those skilled in the art.

Figure 8:
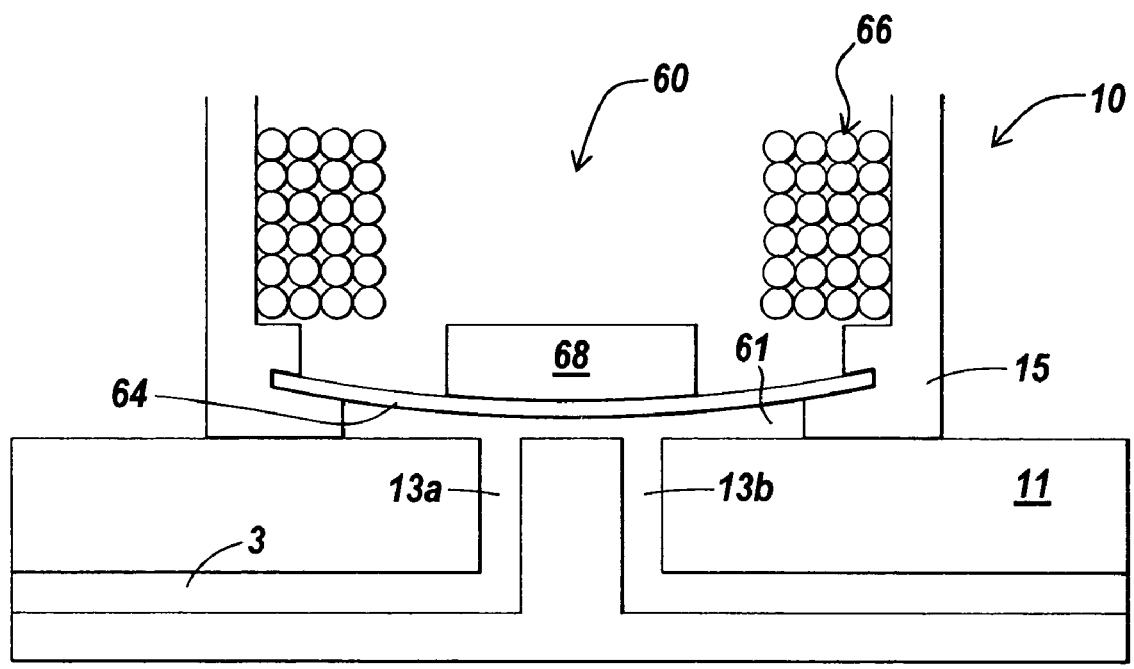
FIG. 8 illustrates an electromagnetic valve incorporated into a microfluidic system according to an embodiment of the invention.

According to another embodiment of the invention, the capping module 15 may be used to incorporate an electromagnetic valve into a microfluidic system. An example of an electromagnetic valve component housed in a capping structure for implementation in a microfluidic system according to the teachings of the invention is shown in FIG. 8. As shown, the electromagnetic module 60 comprises a cap 15 defining an interior chamber 61, a membrane 64 for selectively blocking flow through one or both of the communication ports in the substrate and an actuator assembly for deflecting the membrane 64. According to the illustrative embodiment, the actuator assembly comprises a coil 66 and a magnet 68. One skilled in the art will recognize that other suitable means for deflecting the membrane may be used, including piezoelectric actuators.

The electromagnetic capping module 60 may be stacked on the substrate 11 such that the membrane, when deflected, blocks one or more of the communication ports 13a and 13b. The electromagnetic capping module 60 thus integrates a valve for selectively blocking flow through the channel 3 into the microfluidic flow path. As described above, the electromagnetic capping module may be placed on the substrate using automated "pick and place" equipment or through any suitable means known in the art.

According to yet another embodiment, shown in FIGS. 9–27, the microfluidic component integrated in a capping module may comprise a molecular fractionation element to form a molecular fractionation device that may be coupled to a microfluidic chip to form a molecular fractionation device for segregating biomolecules according to their physical and biological properties, or for reacting, binding or retaining a sample or a selected portion of a sample. The molecular fractionation system can be employed in a variety of applications involved in protein expression analysis, both analytical and preparation, including applications, such as the identification of molecular markers, identification and characterization of protein interactions, examination of molecular basis and profiles of a variety of ailments and delineation of protein structure/function in general. For example, the molecular fractionation system may be used to quantify and identify protein components in a mixture for drug discovery and life science research.

Figure 9:
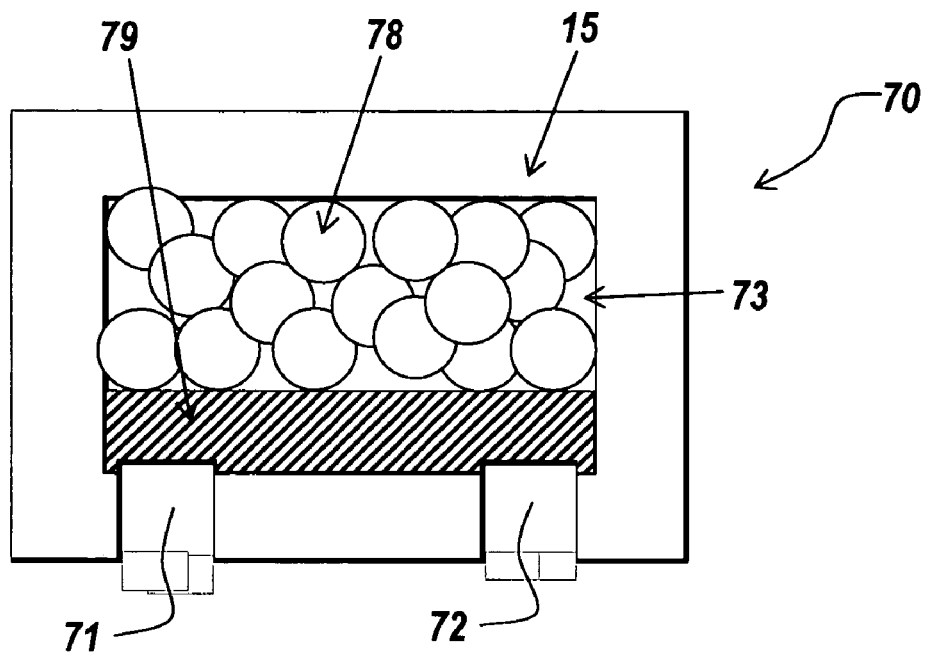
FIG. 9 illustrates a molecular fractionation device formed in a capping module according to an illustrative embodiment of the invention.

According to an illustrative embodiment, the molecular fractionation device is an affinity column 70, shown in FIG. 9, which comprises a capping module 15 that incorporates a matrix 78, such as an array of affinity beads, for segregating a sample into a plurality of fractions. According to the illustrative embodiment, the matrix 78 is accommodated in a chamber 73 of the capping module 15, though one skilled in the art will recognize that the capping module may have any suitable configuration for incorporating a matrix. The matrix 78 has an affinity for a selected component of the sample flowing through the chamber. For example, in one aspect, the matrix 78 binds to a selected component of a sample, while allowing other components of the sample to pass through the device, thereby separating the selected component from the rest of the sample. Alternatively, the matrix 78 can react with or immobilize a selected component of a sample without reacting with or immobilizing other components of the sample. In the embodiment shown in FIG. 9, the capping module 15 includes a chamber 73 for holding the matrix 78 and connector ports 71, 72 for allowing fluid flow into and out of the chamber 73 and for interfacing with communication ports of a substrate or channel. The affinity column 70 may also include a trapping filter 79 for compartmentalizing the matrix 78 within the capping module 15, while allowing sample flow into and out of the chamber 73 via the connector ports 71, 72.

In the embodiment shown in FIG. 9, the chamber 73 has an internal volume of between about one and about ten microliters, though one skilled in the art will recognize that the chamber 73 may hold any suitable volume.

The affinity column 70 easily integrates into an existing microfluidic chip to form a molecular fractionation system for separation and/or processing of a sample without requiring significant or expensive modification of the chip structure. One skilled in the art will recognize that the molecular fractionation device may have any suitable configuration and size, and is not limited to the illustrative affinity column.

Figure 10:
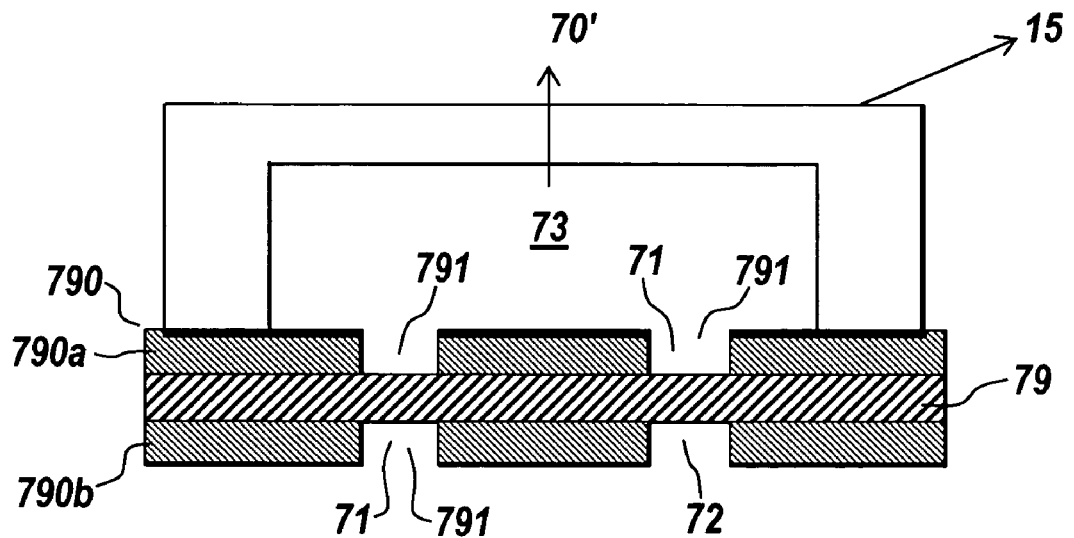
FIG. 10 illustrates a molecular fractionation device formed in a capping module including at least polyester layer, according to an alternate embodiment of the invention.

FIG. 10 illustrates a molecular fractionation device 70' according to another embodiment of the invention, where the device further includes one or more bonding layers for sealing the chamber 73 and preventing leakage. For example, the molecular fractionation device 70' includes a first impermeable layer 790a, and a second impermeable layer 790b bonded to each side of the trapping filter 79.

According to an illustrated embodiment, at least one of the impermeable layers 790a or 790b is formed of polyester film, though one skilled in the art will recognize that any suitable material may be used. In an illustrated embodiment, high strength adhesive, such as 9471LE Adhesive transfer tape acrylic glue from 3M, may be laminated on a both sides of the patterned polyester films to make 125-micron thick polyester bonding layers. The bonding layer or layers 790a, 790b block most of the trapping filter 79 to prevent leakage, while leaving the connector ports 71, 72 exposed through openings 791 in the bonding layers to allow fluid to flow therethrough.

Figure 11A:
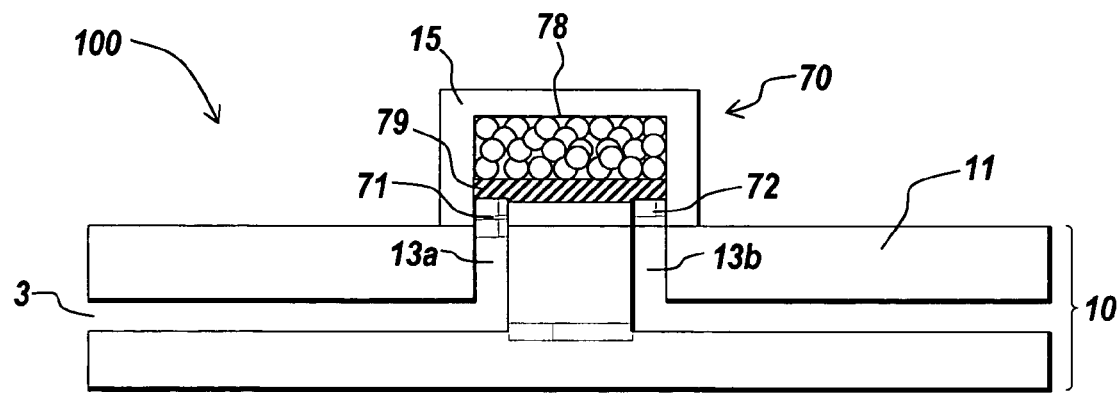
FIG. 11A is side view of the molecular fractionation device of FIG. 9 assembled onto a fluidic chip to form a molecular fractionation system.

As shown in FIG. 11A, an affinity column 70 may be coupled to a basic fluidic chip 10, such as the chip 10 of FIG. 1 to form a molecular fractionation system 100. The connector port 71 of the affinity column 70 aligns with the communication port 13a of the substrate, and the connector port 72 aligns with the communication port 13b, to form a closed fluid path through the affinity column 70. The affinity column 70 thus integrates the ability to segregate or fractionate a sample using the matrix 78 into the basic fluidic chip 10.

Figure 11B:
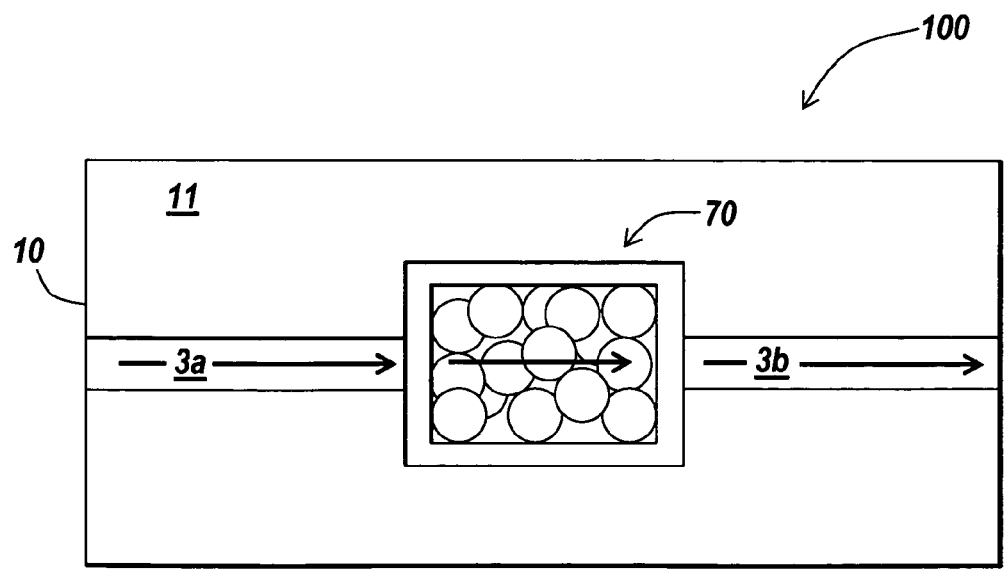
FIG. 11B is a top view of the system of FIG. 11A.

The capping module 15 may be designed with any suitable number of connector ports to provide one or more fluid paths through the affinity column 70. For example, as shown in FIG. 11B, which is an overhead view of the assembled molecular fractionation system 100 of FIG. 11A, the capping module 15 may have two connector ports 71 and 72, which connect the channels 3a, 3b, respectively, to the chamber 73. The two-port capping module thus forms one fluid path through the affinity column, comprising the channels 3a, 3b and the chamber 73 of the capping module 15.

Figure 12A:
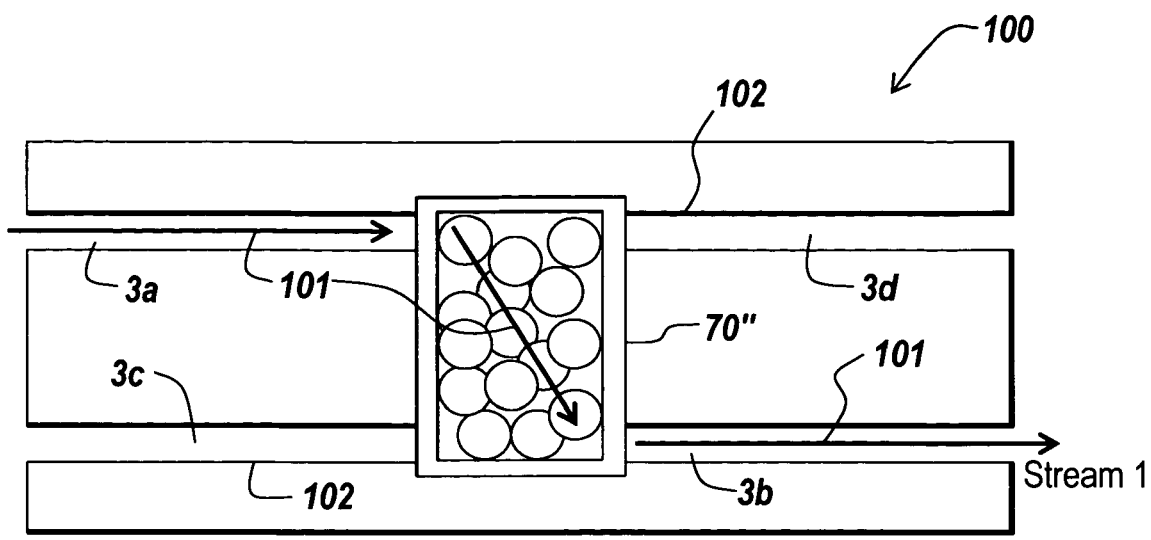
FIG. 12A is a top view of a molecular fractionation system including a four-port capping module.
Figure 12B:
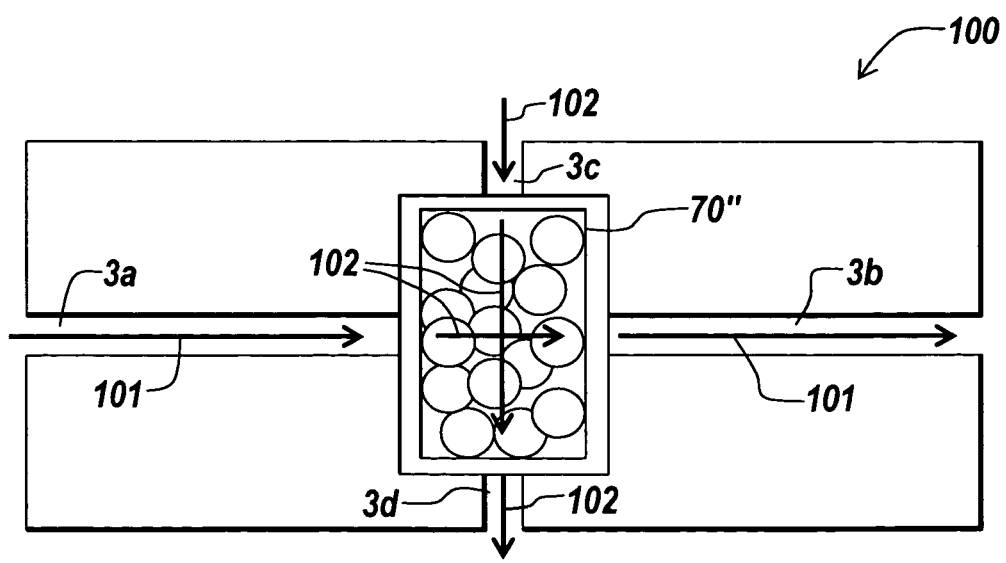
FIG. 12B is a top view of a molecular fractionation system including a four-port capping module according to another embodiment of the invention.

As shown in FIGS. 12A and 12B, a molecular fractionation system 100 formed by a four-port affinity column 70" has two flow paths through the affinity column 70". The first flow path 101 and second flow path 102 may comprise parallel channels, as shown in FIG. 12A, or channels that are perpendicular to each other, as shown in FIG. 12b. In the embodiment shown in FIGS. 12A and 12B, the first flow path 101 may be used to flow sample from a first channel 3a through the trapping filter 79, across the matrix 78 and out through the trapping filter 79 again to a second channel 3b. The second flow path 102 connects a third channel 3c to a fourth channel 3d through the chamber 73 or recess of the capping module 15. The second flow path 102 may be used for elution, for example, by flowing an elution buffer along the second flow path through the matrix 78 starting before and ending after the sample flows through the column. The elution buffer thus rinses the entire matrix 78 coated by the sample.

One skilled in the art will recognize that an affinity column formed according to the teachings of the present invention may have any suitable number connector ports and flow paths, depending on the desired application.

The capping module may comprise any suitable configuration for accommodating a matrix and is not limited to the illustrative embodiments. For example, according to another embodiment, an affinity column 70 may comprise a capping module, such as the capping module shown in FIG. 4, that includes a first connector port 37 and a second outlet port 33 disposed beside and in communication with a central recess 36.

A micro-scale affinity column 70 of an illustrative embodiment of the present invention can be designed to have a volume capacity of between about 1 ul and about 20 ul and size of less than 1 cm$^2$. A plurality of columns may be assembled onto glass microfluidic plates in fluid communication, which can provide a column-to-column dead volume of less than about 100 nl. The present invention may also provide large form factor microfabricated capillary electrophoresis column arrays with 20 cm column length.

One skilled in the art will recognize that the path length, volume of sample in the cap, the number of connector ports and resulting of flow paths and the configuration of the cap can be varied and used to optimize the capturing ability of the matrix for a desired sample.

The matrix 78 is selected based on the biochemical properties of a sample fraction, such as a protein, to be analyzed. According to one embodiment, the matrix 78 filling the micro-scale affinity column comprises conventional affinity column beads known in the art. In the illustrative embodiment, the matrix 78 comprises an array of affinity beads, such as 100 um sephadex, separose, glass or other beads with off the shelf derivitization chemistries, though one skilled in the art will recognize that any suitable material may be used to form the matrix 78. Examples of suitable chemistries include, but are not limited to: antibodies, small and large molecule ligands, molecular "baits" and transport molecules, such as abumin.

Figure 13:
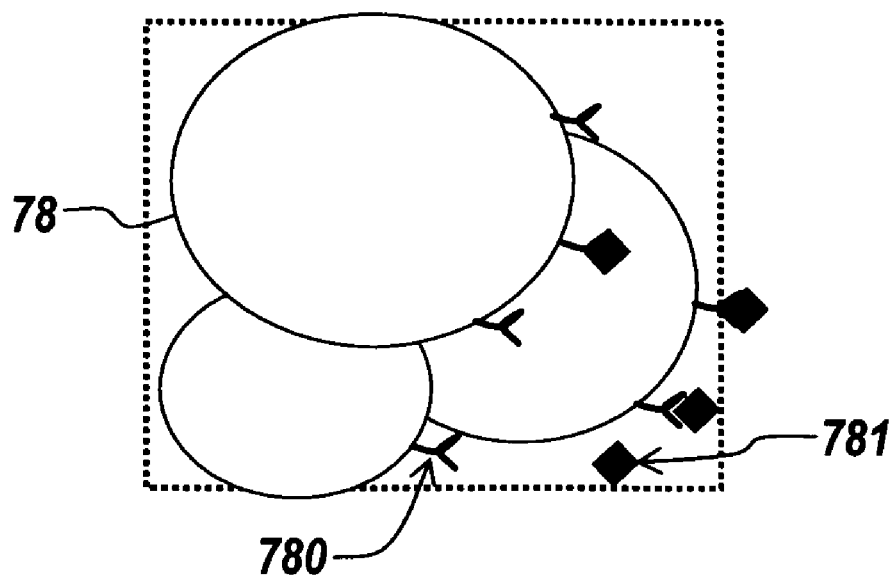
FIG. 13 is a detailed view of the matrix of the molecular fractionation device of FIG. 9.

As shown in FIG. 13, the illustrative matrix 78 may comprise beads, which are coated with useful binding sites 780 for trapping certain molecules 781 that flow through the affinity column. For example, matrix may comprise affinity beads, comprising biologically specific ligands covalently linked to a chromatography matrix. The "capacity" of the matrix for trapping molecules corresponds to the number of accessible binding sites. Once the capacity is reached, the matrix 78 does not continue to trap molecules. In the illustrative embodiment, the matrix beads bind between about 5–25 mg per ml of column material. Therefore, a micro-scale affinity column 70 of 5 ul will bind between about 25 ug to about 125 ug of a sample, an amount very comparable to what is commonly loaded on analytic 2DE gels.

The specific matrix 78 disposed in the capping module 15, may be selected based on the affinity of certain biomolecules in complexes. For example, lectin-coated beads can be used study glycoprotein. In another example, beads with trypsin can be used to prepare peptide for mass spectroscopy analysis. The matrix may also comprise a reverse phase matrix (e.g. C18, C8 or C4 matrix), a normal phase matrix, ion exchange (anion or cation matrix) and other types of affinity separations (antibody, ligand, etc). The primary separation of proteins may be performed by adsorption followed by elution. Specific protein from the crude sample is retained on the beads and is eluted off by changing the buffer condition either in steps or by a linear gradient. One of ordinary skill in the art will be able to determine an appropriate type and amount of matrix for performing a desired function.

Based on the experimental need of protein separation, purification and identification, a capping module 15 for a molecular fractionation device 70 can be microfabricated for any of a number of processes. For example, the capping module 15 may be microfabricated for binding activity, wherein binding properties of biological molecules to specifically charged matrix can be used either for adsorption separation or for sample enrichment. For example, the capping module may be designed for adsorption separation. In adsorption separation, the matrix is coated with ligands that can be used for identification and separation of particular protein, a class of protein or a family of protein. The capping modules may be prepared by preloading the beads charged with ligands, dyes, antibodies, etc for affinity purification. For example, the capping module 15 may include lectin beads for glycoproteins, antibodies to study particular protein/protein family. The matrix 78 may also be designed for sample enrichment, for example by using reverse phase beads—such as C18 for binding short peptides, C8 or C4. The capping module 15 may be used for a wash/buffer exchange or as a filter station, wherein a transverse filter unit can be used to exchange buffer and concentration in between different Adsep processes. The matrix may include enzymes on the matrix surface that react with selected fractions of the sample. For example, the matrix 78 may be selected for enzymatic activity, such as by using Trypsin beads for Trypsin digestion or for signal detection, using Luciferase beads.

One skilled in the art will recognize that alternative beads, alternate linking chemistries, and alternate choices of a binding molecule to capture any given target may be used, which are known to those of ordinary skill in the art.

Figure 14:
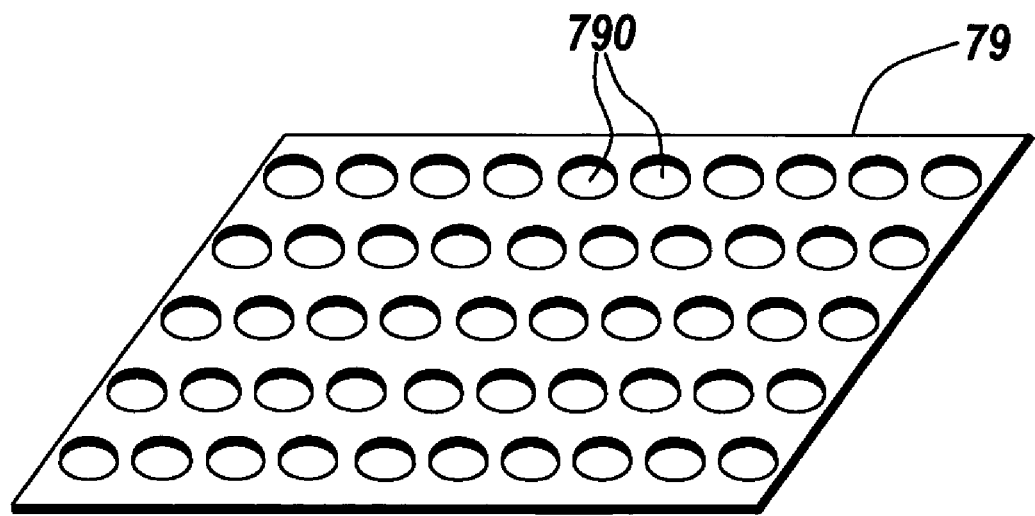
FIG. 14 is a detailed view of the trapping filter of the molecular fractionation device of FIG. 9.

The semipermeable trapping filter 79, which compartmentalizes the matrix 78, is preferably impermeable to the matrix 78, but permeable to the flow of liquid and certain molecules. For example, as shown in FIG. 14, the trapping filter 79 may comprise a membrane formed of any suitable material including holes 790 that are smaller than components of the matrix 78, for example, the beads, to prevent passage of the matrix through the trapping filter 79 while permitting flow of sample and reagents therethrough. The trapping filter 79 thus allows sample flow to pass from the associated chip ports; through the chamber 73 and across the matrix 78, and back again to the chip. The trapping filter 79 prevents the beads or other matrix components from flowing across the trapping filter 79, but allows protein solutions, and other samples to flow freely across the filter 79.

The modular design of a molecular fractionation device 70 using capping modules 15 with a compartmentalized matrix 78 of desired chemistry integrated with microfluidic plumbing and valves on a microfluidic chip 10 provides unique capabilities for sample handling and resolution enhancement. Capping modules 15 can be individually designed and coupled to the plumbing layer of the chip 10 to achieve a number of desired effects. Glass chips with appropriate plumbing can be prepared with molecular fractionation devices, such as affinity columns, attached permanently. Alternatively, specialized molecular fractionation systems formed using capping modules can designed to be removable and replaced by other capping modules on same set of microfluidic plumbing.

To fabricate an affinity column 70, the trapping filter 79, which comprises a membrane permeable to liquids and molecules in the illustrative embodiment, is bonded over a recess or chamber formed in a capping module 15. Alternatively, one or more bonding layers 790 are also bonded to the matrix and/or capping module. The matrix 78, illustrated as an array of affinity beads, may be injected and sealed into the channel in the capping module 15. The assembled affinity column 70 is mounted on a microfluidic substrate including channels formed therein, so that connector ports of the affinity column align with the communication ports in the substrate 11, for example, as shown in FIG. 11A.

A large number of affinity columns or other microfluidic components may be manufactured through a batch process that makes an array of microfluidic elements in capping modules at a time. For example, in one embodiment, a 3×3 array of affinity columns 70 may be assembled in a batch to make nine affinity columns at a time.

According to one embodiment, an affinity column 70 may be manufactured by inserting the matrix 78 into the capping module 15 during the manufacturing process. Later, the manufactured affinity column 70 including the matrix is assembled onto a basic fluidic chip 11, for example, as shown in FIG. 11A. Liquids are added to the system after assembly of the affinity column 70 thereon, and the integrated system operates at a later time. A benefit of such a manufacturing process is for instances when the manufacturing of the basic fluidic chip 11, such as for glass or silicon basic fluidic chips, takes much longer than the assembly process. The application shown in FIG. 11A is also beneficial for applications in which the same basic fluidic chip 11 may be used with a wide variety of molecular fractionation devices 70 defined by their trapped matrix 78. Many basic fluidic chips may be built and then "programmed" by assembly with one or more desired molecular fractionation devices in a quick and flexible last step in the manufacturing of the whole system.

According to another embodiment, for example, as shown in FIGS. 15a–d, an affinity column 70 can built and stored without a matrix 78, and subsequently assembled onto a basic fluidic chip 10 without the matrix disposed in the capping module 15. The matrix 78 is added to the capping module 15 after assembly of the affinity column onto the chip substrate 11. After adding fluid to the chip 10, the matrix 78 flows through a loading channel 3e formed in the substrate 11 and into the chamber 73 via a matrix insertion port 150. As shown in FIG. 15c, the matrix insertion port 150, which is provided in addition to the connector ports 71, 72, is open and uncovered by the trapping filter 79, so that the matrix may freely flow into the capping module 15. An advantage of loading the matrix after assembly onto the fluidic chip 11 is that the matrix may also be unloaded in a similar manner and subsequently re-loaded with a different matrix during the use of the system.

Figure 16:
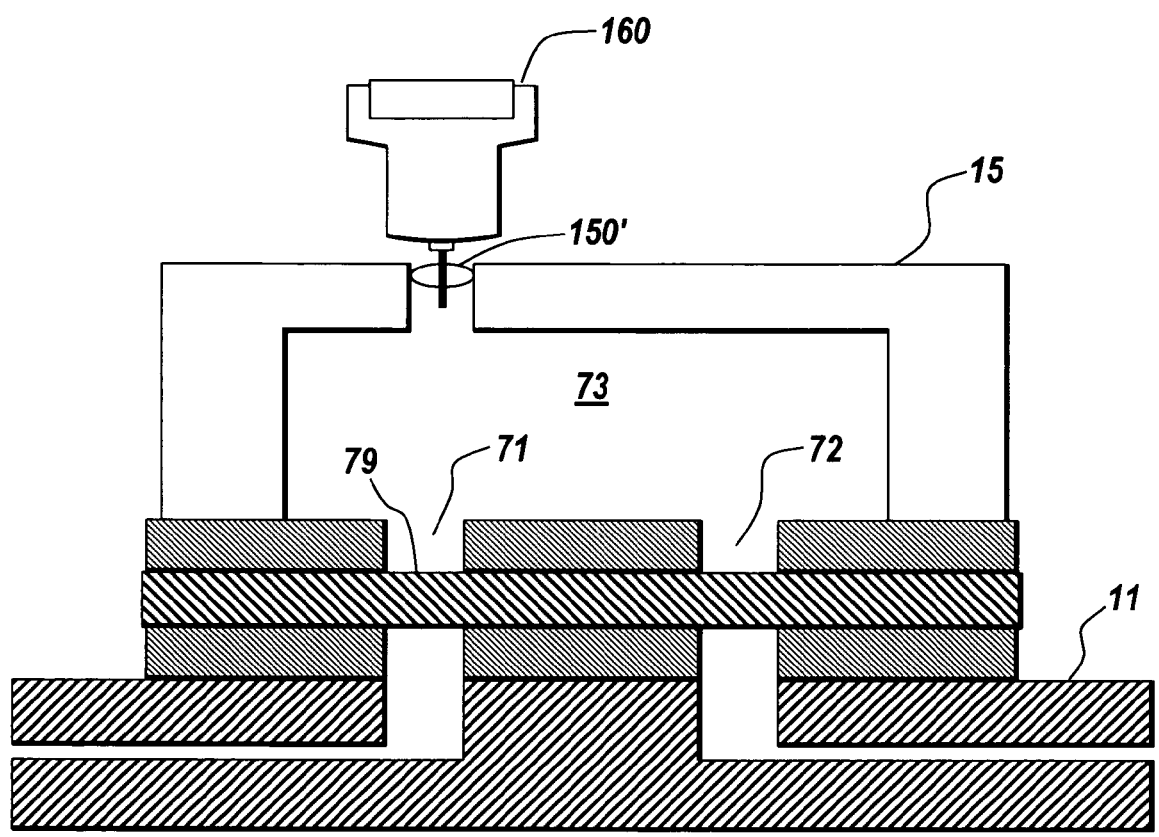
FIG. 16 illustrates a molecular fractionation device having a matrix loading port on the top of the device according to another embodiment of the invention.

According to one embodiment of the invention, shown in FIG. 16, a matrix insertion port 150' for loading a matrix 78 into a capping module, can be located on the top wall of the capping module 15. A matrix 78 may be injected into capping module interior via the matrix insertion port 150' using a syringe 160 or other suitable device. The matrix insertion ports 150 or 150' may be closed and sealed after matrix loading. One skilled in the art will recognize that any suitable means for loading a capping module with a matrix may be used in accordance with the teachings of the invention.

Figure 17A:
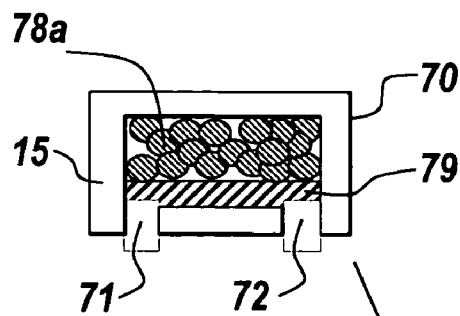
FIGS. 17A–17C illustrates a manufacturing process for a molecular fractionation device according to another embodiment of the invention, wherein the matrix of the molecular fractionation device is chemically modified after manufacture.
Figure 17B:
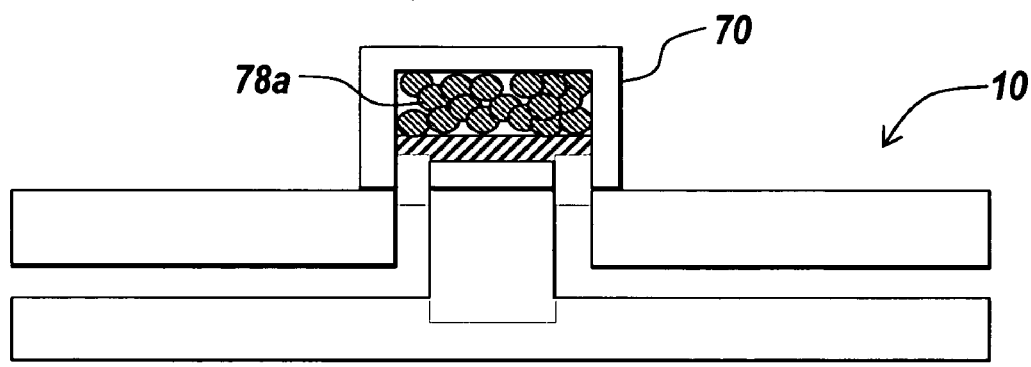
Figure 17C:
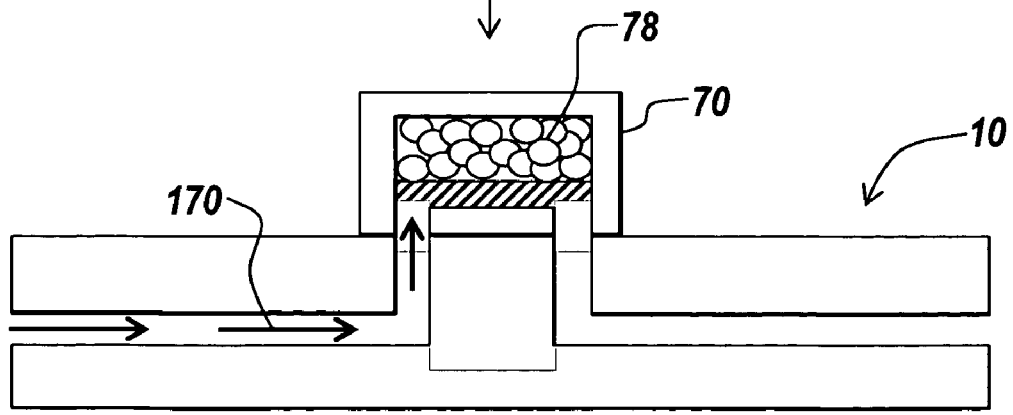

According to another embodiment, the affinity column 70 forming the molecular fractionation system may be built with a precursor matrix 78a, as shown in FIG. 17a. The precursor affinity column may then be assembled onto the basic fluidic chip 10, as shown in FIG. 17b, and the matrix may subsequently be chemically modified in situ, as shown in FIG. 17c. The precursor matrix 78a can be modified by flowing modifying chemistry 170 over the precursor matrix 78a, which reacts with the precursor matrix to form the final matrix 78 to be used. For example, in one embodiment, the precursor matrix 78a comprises beads that are pre-coated with biotin. After the precursor matrix is assembled in the capping module 15, antibody bound to streptavidin flows over the beads and the streptavidin-biotin bond then ties the antibody to the trapped bead matrix. An advantage of modifying the matrix in situ is the ability to re-program, reset or customize the matrix during use of the system, so that the matrix may be used for a variety of applications.

Figure 18A:
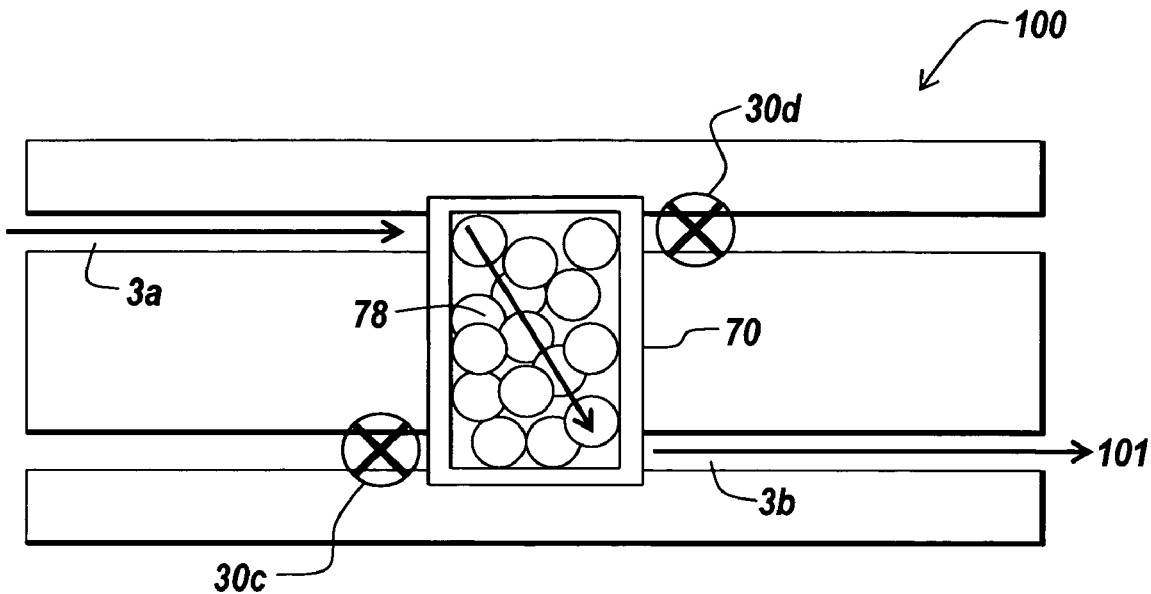
FIGS. 18A and 18B illustrate a molecular fractionation device according to one embodiment of the invention, wherein the device is used to capture a fraction of a sample.
Figure 18B:
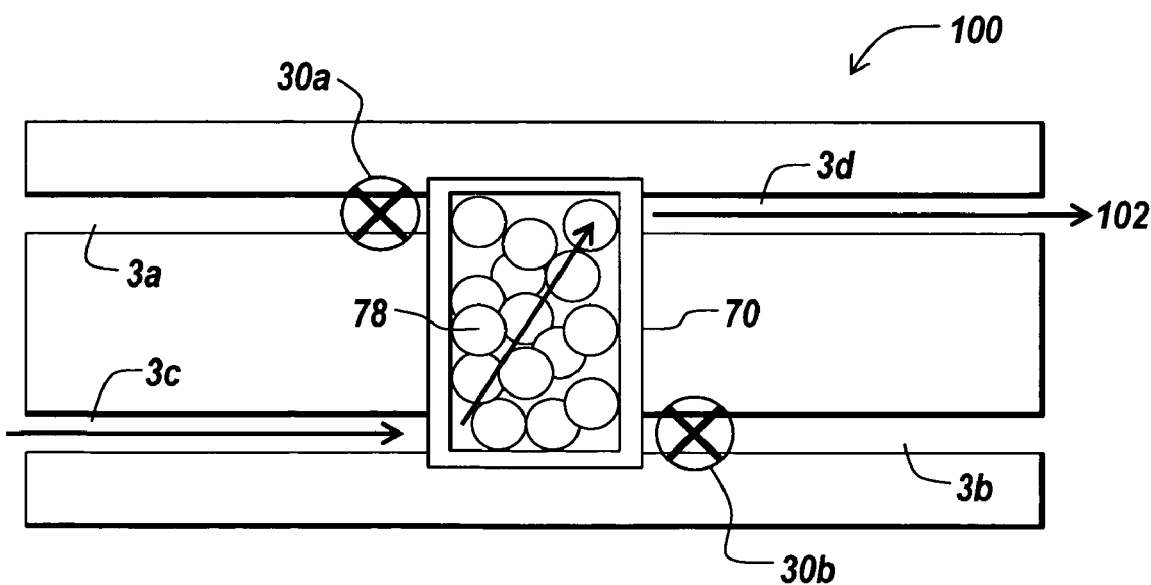

A molecular fractionation device of the present invention, such as the illustrative affinity column 70, has a number of applications and may be used to perform a number of different microfluidic functions according to various embodiments of the present invention. For example, as shown in FIGS. 18a and 18b, a molecular fractionation system 100 formed using an affinity column 70 coupled to a microfluidic chip 10 may be used to separate and capture a fraction in a sample from other components in the sample. For example, the molecular fractionation system may be used to separate and capture selected molecules in a sample. The molecular fractionation system 100 captures the selected molecules by first passing a buffer containing the sample from a sample inlet channel 3a through an affinity column 70 containing a matrix 78 configured to bind with the selected molecules, as shown in FIG. 18a. The fraction of the sample that binds to the matrix, i.e., the selected molecules, are trapped within the affinity column 70 by the matrix 78, while other components flow through the affinity column and out a first outlet channel 3b. As show, the channels 3c, 3d forming the second fluid path can be selectively closed during the first step using valves 30c, 30d, or other suitable flow restricting device.

In a second step, shown in FIG. 18b, the second fluid path valves 30c, 30d open, valves 30a, 30b, or other flow restricting devices, in the channels 3a, 3b of the first fluid path close to block flow through the first fluid path. In the second step, the system passes a suitable release solution from a second inlet channel 3c, through the column 70. The release solution breaks the binding between the trapped sample fraction and the matrix 78. The release solution then releases the sample fraction into the second outlet channel 3d, which is separate from the first outlet channel 3b where the rest of the sample exits. The two step procedure shown in FIGS. 18a and 18b thus extracts one fraction of the sample (determined by the chemistry on the matrix) from a first flow path 101 defined by channels 3a and 3b to a second flow path 102, defined by channels 3c and 3d. The fraction that is fractionated can be controlled based on the type of matrix 78 within the capping module 15. One skilled in the art will recognize that a plurality of fractions of a sample may be retained by the matrix.

Figure 19C:
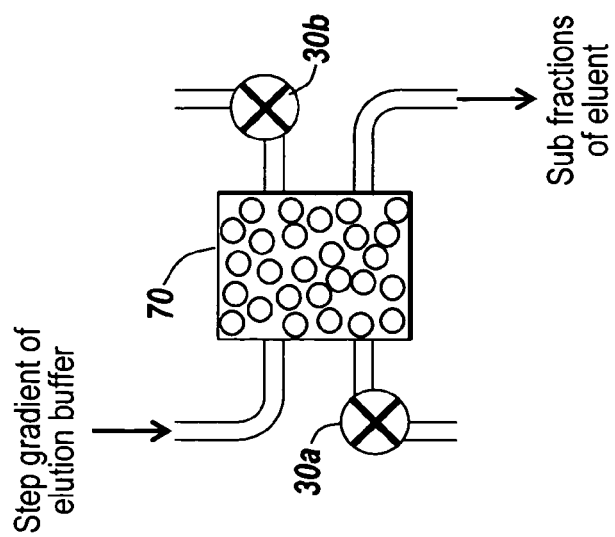
FIGS. 19A–19C illustrate another application of the molecular fractionation device of an illustrative embodiment of the invention, wherein the device is used to capture and elute a sample fraction.
Figure 19B:
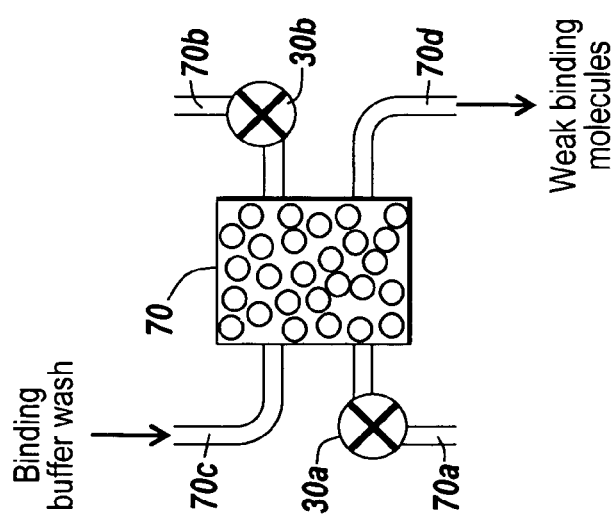
Figure 19A:
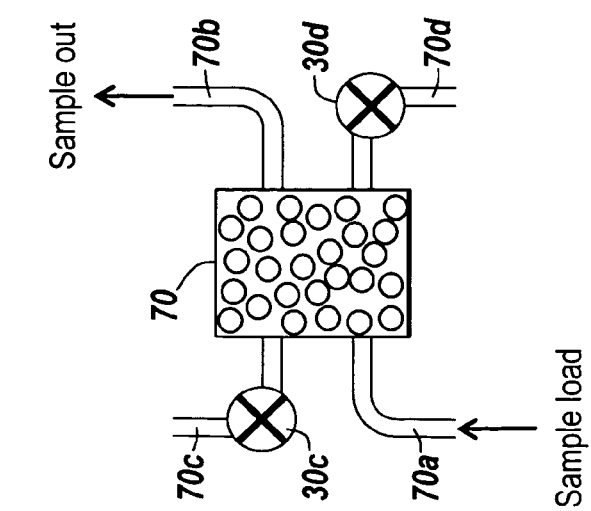

According to another application, shown in FIGS. 19A, 19B and 19C, a molecular fractionation system 100 may be used to capture and elute a sample or a fraction of a sample. The capture and elution method comprises a first step, show in FIG. 19A, of loading a sample, for example, by flowing a sample through a molecular fractionation device, such as an affinity column 70, from a first inlet channel 3a (inlet sample channel) to a first outlet channel 3b (sample outlet channel), as shown in FIG. 19A. In the first step, the first inlet channel 3a and the first outlet channel 3b are open to allow fluid flow therethrough, while the second inlet channel 3c and the second outlet channel 3d are closed by valves 30c, 30d, or any other suitable flow-restricting device. The matrix 78 traps the sample, or a selected fraction of the sample, while the remaining components of the sample flow through the first outlet channel 3b.

In an optional second step, a binding buffer wash can be performed to flush weak binding molecules from the matrix, as shown in FIG. 19B, by flowing a binding buffer through the fluid path formed by the second inlet channel 3c and the second outlet channel 3d. In this step, the first inlet channel 3a and the first outlet channel 3b can be closed or blocked using valves 30a, 30b, respectively, or any other suitable flow-restricting device.

In a third step, shown in FIG. 19C, an operation of gradient elution is performed, similar to an elution process of a macro scale column, to separate the sample or sample fraction trapped by the matrix 78 into a plurality of subfractions. In the illustrative embodiment, a step-wise gradient of an eluent buffer is followed, illustrated in the graph of FIG. 20A, to vary the chemical composition of the buffer. The eluent buffer flows across the affinity column 70 from a second inlet channel 3c (elution inlet channel) to a second outlet channel 3d (release channel). As the concentration of the eluent rises, different molecules in the trapped fraction are released off the matrix 78 as bands of different affinity and flow out the "release" channel 3d.

Figure 20A:
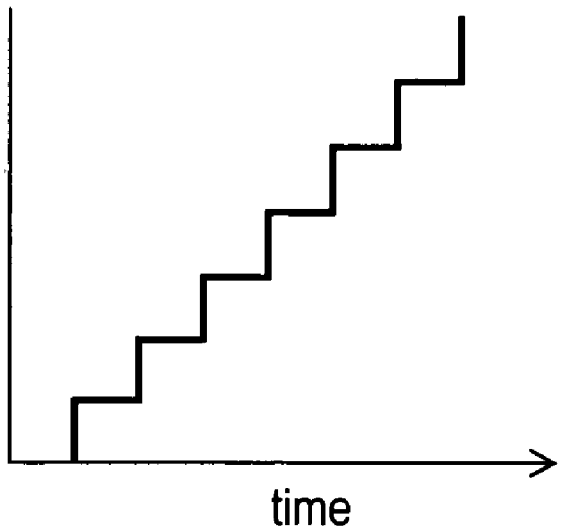
FIGS. 20A and 20B are graphs illustrating the elution process of FIG. 19C.
Figure 20B:
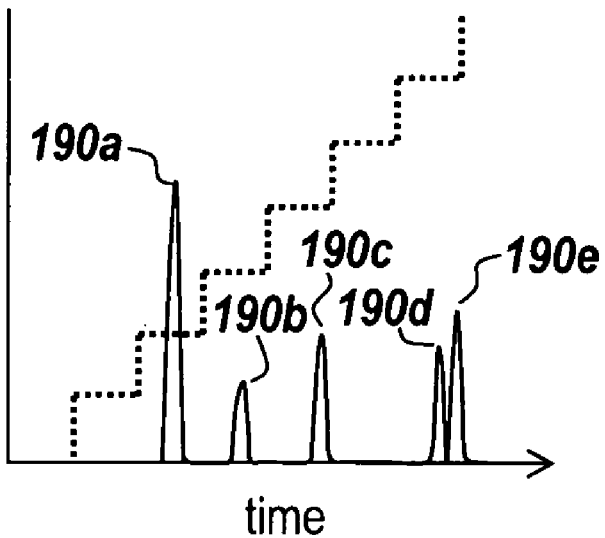

FIGS. 20A and 20B are graphical illustrations of the elution of the bands of the trapped sample or sample fraction over time, as a result of the step-wide gradient through the affinity column. In the graph, each peak 190a, 190b, 190c, 190d, 190e, corresponds to a sub-fraction of the sample as the sub-fraction elutes from the matrix. One skilled in the art will recognize that the invention is not limited to a step-wise gradient and that a continuous gradient elution can also be performed in the molecular fractionation system of the illustrative embodiment.

Figure 21:
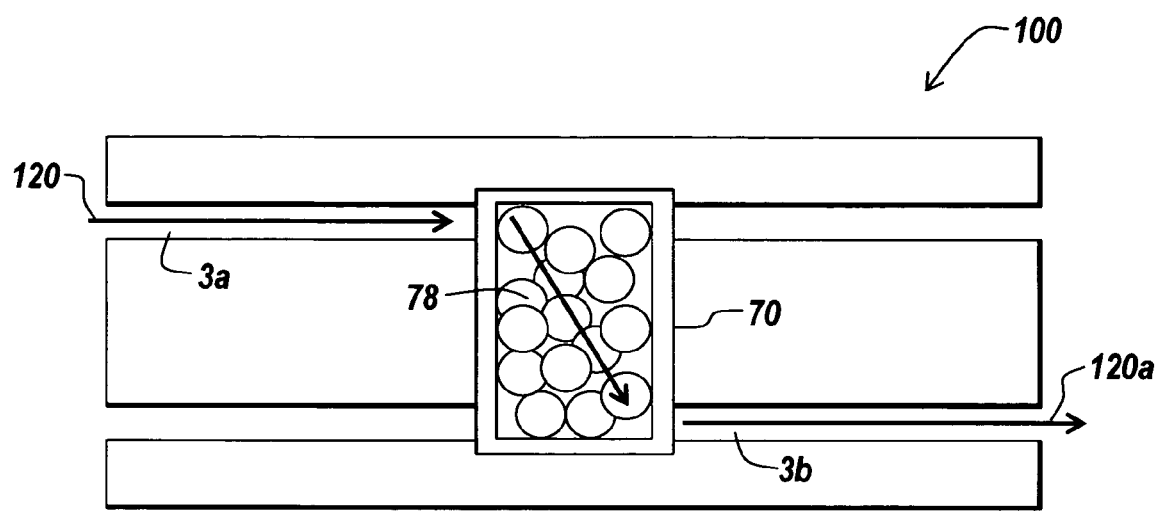
FIG. 21 illustrates a reactive molecular fractionation device according to another application of the present invention.

According to another application, a molecular fractionation system 100 may be used to process a sample 120 in a flow stream, as shown in FIG. 21. In the "reaction" molecular fractionation system, the matrix 78 includes enzymes or reactants on the matrix surface that react with selected fractions of the sample to form a reacted sample 120a. To perform a reaction using the reaction molecular fractionation system, a buffer containing the sample first flows from an input channel 3a and through the affinity column 70. The enzymes on the matrix surface 78 react with and process certain fractions of the sample. The reacted sample then flows to an outlet channel 3b. For example, according to one embodiment, the matrix 78 can be coated with trypsin, and a protein sample flows across the column 70. The output stream of the column 70 in outlet channel 3b then contains trypsin-digested proteins (i.e., peptide fragments of the input proteins).

Figure 22:
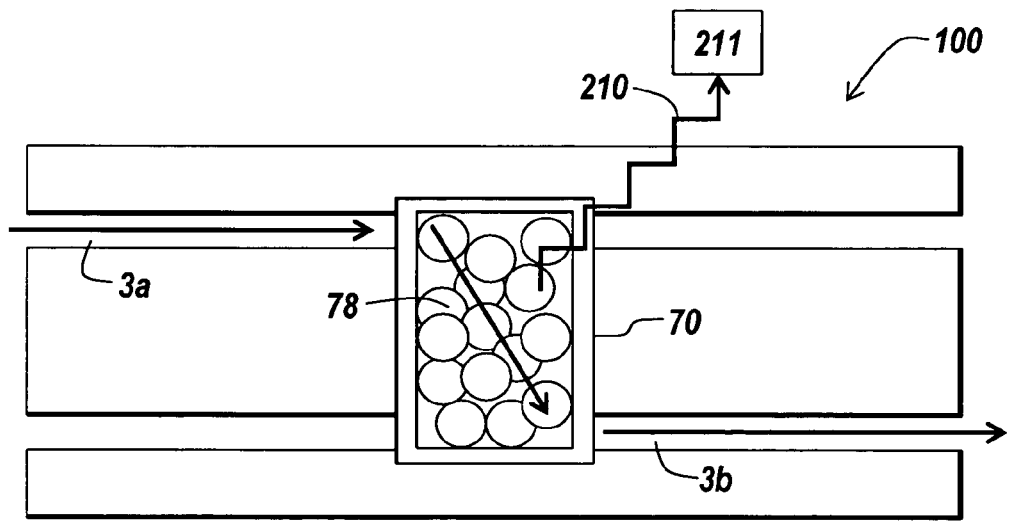
FIG. 22 illustrates a molecular fractionation device used to detect a property of a sample, according to another embodiment of the invention.

According to another application, an affinity column 70 forms a molecular detector, as shown in FIG. 22. In the embodiment shown in FIG. 22, the matrix 78 contains detection molecules that react with a sample to produce a detectable signal, such as light, or bind to the sample to produce shifts in optical fluorescence or optical absorbency of the molecules in the affinity column 70 to form a "transduction" molecular fractionation system for detecting a parameter of the sample. For example, the illustrated molecular detector may be used to determine a quantity of a sample flowing through a channel 3a. In the embodiment shown in FIG. 22, buffer containing a sample flows from the channel 3a through the column 70. As the sample contacts the matrix 78 within the affinity column 70, the matrix 78 produces a measurable reaction, indicated by arrow 210, which allows an external detector 211 to determine the quantity of the sample. According to one embodiment, a luciferin-luciferase system may be placed in the matrix, which emit photons when an ATP molecule from the flow stream is converted. The photons may be measured to determine the quantity of ATP present in the input flow stream. After passing through the matrix 78, the sample may flow through an outlet channel 3b.

Figure 23A:
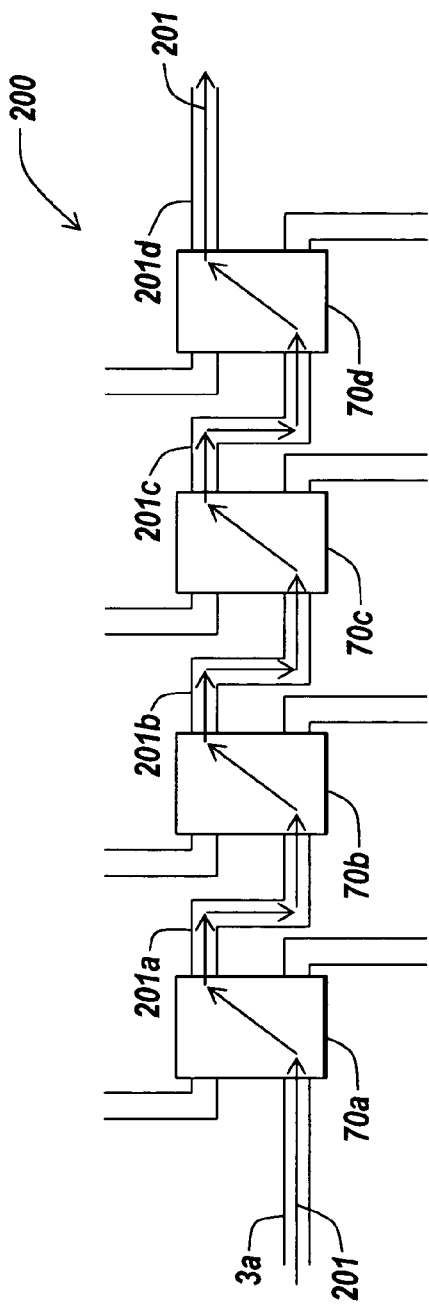
FIGS. 23A and 23B illustrates a sample fractionation system comprising a plurality of molecular fractionation devices in series for separating a sample into a plurality of fractions.
Figure 23B:
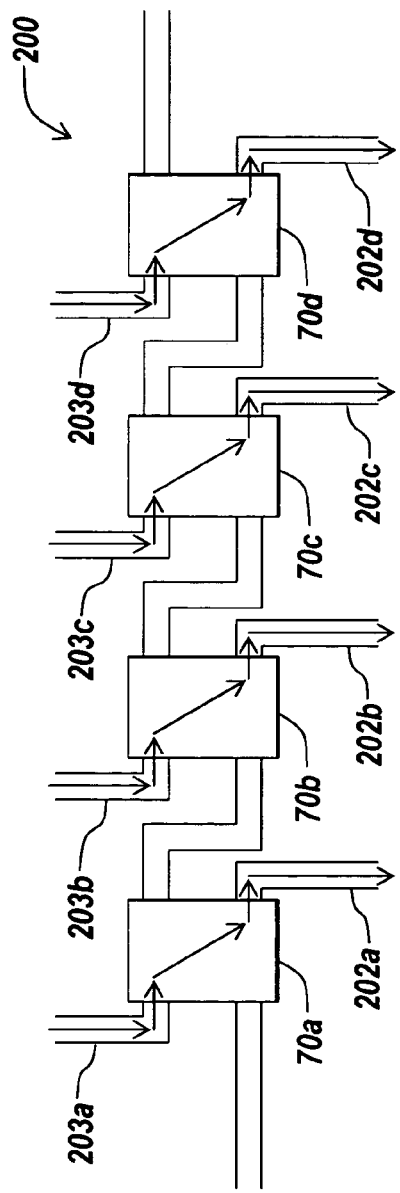

According to yet another application, a sample fractionation system 200, shown in FIGS. 23A and 23B, includes a plurality of affinity columns 70a, 70b, 70c, 70d or other molecular fractionation devices, arranged in series on a single basic fluidic chip to extract fractions from a single channel 201. For example, the sample fractionation system 200 may separate a sample into several fractions, by configuring each affinity column 70a, 70b, 70c, and 70d to retain a selected fraction of the sample. Each affinity column 70a, 70b, 70c, and 70d includes a matrix 78 configured to bind to and retain a selected fraction of the sample. Each affinity column shown in FIGS. 23A and 23B is a four-port column, having at least two inlet ports and at least two outlet ports, though one skilled in the art will recognize that the invention is not limited to four-port columns. As shown, the affinity columns are arranged so that they are serially connected to a single sample flow path 201 comprising a plurality of connecting channels 201a, 201b, 201c, 201d formed in the substrate of a chip. Each connecting channel connects a first outlet port, i.e., a sample outlet port of each affinity column 70a, 70b, 70c or 70d to a first inlet port (i.e., a sample outlet port) of an adjacent affinity column 70, such that a sample passes through each of the affinity columns 70a, 70b, 70c, 70d successively, with each affinity column 70a, 70b, 70c, and 70d retaining a selected portion of the sample. Each affinity column 70a–70d is separately connected to a corresponding elution or release flow path 202a–202d, respectively, through a second outlet port, i.e., an elution outlet port.

To fractionate the sample into a plurality of fractions, the sample flows through the sample flow path 201 (indicated by the arrows), passing serially through the each of the four illustrated affinity columns 70a, 70b, 70c, 70d, as shown in FIG. 23A. A first fraction of the sample binds to and is retained by the first affinity column 70a. The remaining mixture continues to flow serially through the second, third and fourth affinity columns 70b, 70c and 70d, respectively. Each affinity column binds to and retains a corresponding fraction of the sample.

In a second step, shown in FIG. 23B, the system passes a solution from a plurality of inlet elution channels 203a–203d, each of which is associated with an affinity column in the array, through each affinity column 70a–70d via a second inlet port (i.e., an elution inlet port), to the release flow paths 202a–202d, respectively. The solution releases the retained fractions into separate flow streams 202a–202d. The separated fractions can then be collected or further processed. In general, the chemistry of the binding sites on each matrix determines both which types of biomolecules will bind and be retained in the sample buffer and also what other buffers or compounds will reduce the affinity of the biomolecules for the binding sites and thus cause biomolecule release.

One skilled in the art will recognize that the sample fractionation system 200 may comprise any suitable number of molecular fractionation devices, such as the illustrated affinity columns 70, arranged in series and that the sample fractionation system is not limited to the illustrative embodiment.

Figure 24A:
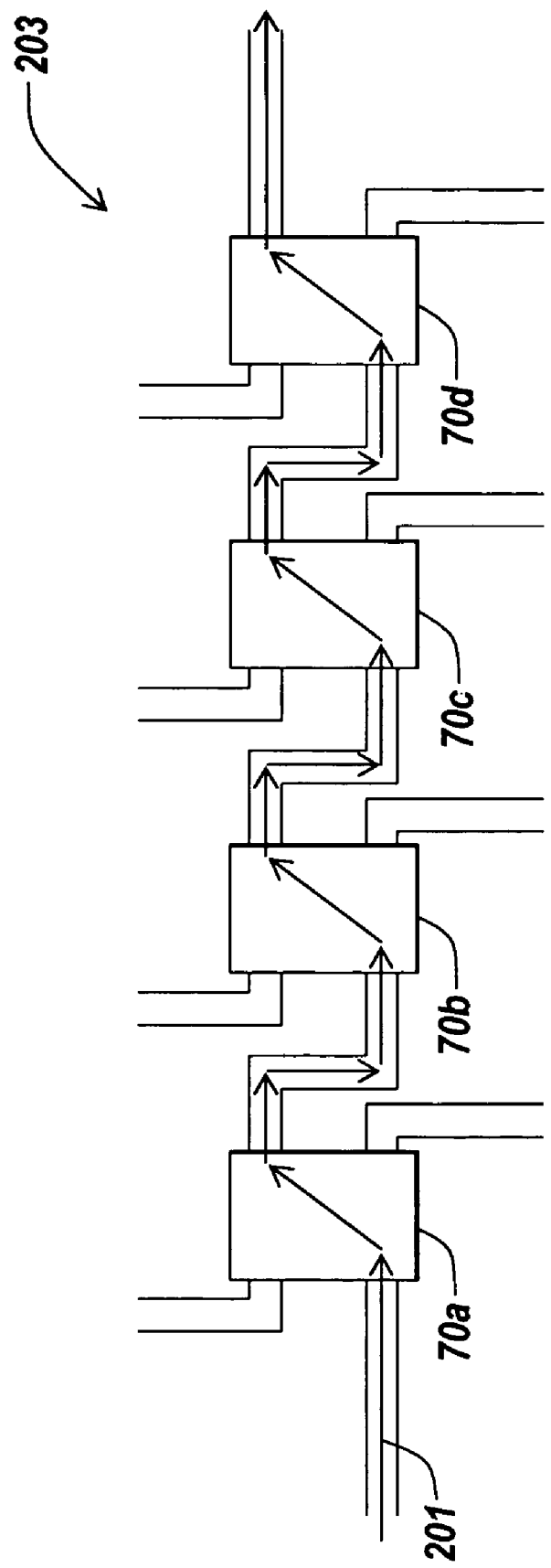
FIGS. 24A and 24B illustrates a two-dimensional sample fractionation and elution system according to another embodiment of the invention
Figure 24B:
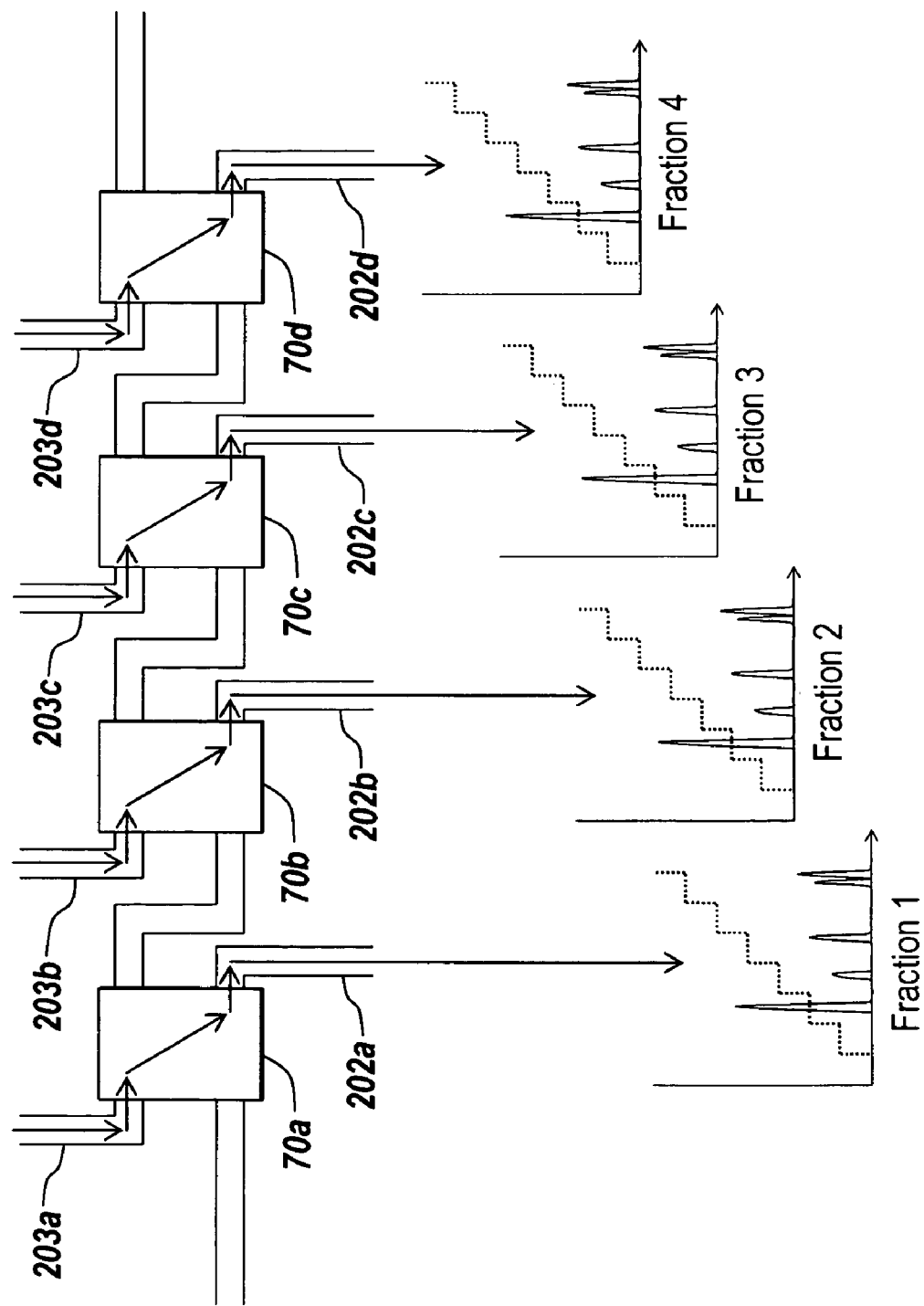

In yet another application, FIGS. 24A–24B show a two-dimensional fraction elution system 230 formed using a plurality of molecular fractionation devices of an illustrative embodiment of the present invention. The fractionation-elution system of FIGS. 24A and 24B implements a full two-dimensional separation or fractionation method, which is combined from sample fractionation and capture-elution methods. Along a first sample flow path 201, an initial input sample mixture is fractionated into a plurality of fractions based on the binding affinity of each fraction to a particular affinity column, as described above, with respect to FIG. 23A. Then, each trapped fraction on each affinity column in the array is separated into a plurality of bands of different affinity by a step gradient elution or a continuous-gradient elution. By performing two stages of fractionation, the two-dimensional fraction elution system 230 provides a high degree of resolution.

As shown, to perform the two-dimensional fraction elution, the sample flows through all the affinity columns 70a–70d in a sample-serial array, as shown in FIG. 24A. A fraction of the sample is loaded onto each affinity column 70a–70d, as each affinity column retains a corresponding fraction of the sample, depending on the chemistry of the associated matrix 78. After loading of the sample fractions onto the affinity columns 70a–70d, elution of each fraction takes place by flowing and varying the concentration of an elution buffer flowing through each affinity column, as shown in FIG. 24B, from an elution channel 203a–203d. The elution buffer thus separates each corresponding trapped fraction into a plurality of bands of different affinity, as shown in the graphs of FIG. 24B. The bands elute from the associated affinity column at separate times and flow through the corresponding release channel 202a–202d. Each of the eluted bands can then be collected or processed further.

In an alternate embodiment of a two-dimensional fraction elution system, a first affinity column 70n is loaded with a first fraction, then the eluted bands from the first column form the sample input to the next affinity column 70n+1 in the series. For example, the two-dimensional fraction elution system can provide a breakdown of a cytokine class into phosphorylated and non-phosphorylated subsets. For example, the two-dimensional fraction elution system can give a breakdown of the cytokine class into phosphorylated and non-phosphorylated subsets by having a first affinity column 70n configured to capture cytokines. The system includes second and third affinity columns 70n+1 and 70n+2, respectively, which capture tyrosine-phosphorylated proteins and serine/threonine-phosphorylated proteins from the eluted cytokines band from the first affinity column 70n.

A two-dimensional fraction elution system 230 with, for example, ten different affinity columns 70 and able to generate twenty step gradients, has a total of two-hundred different "fractionation" bins for one measure of resolution, i.e., the system can produce up to two-hundred different bands.

Figure 25A:
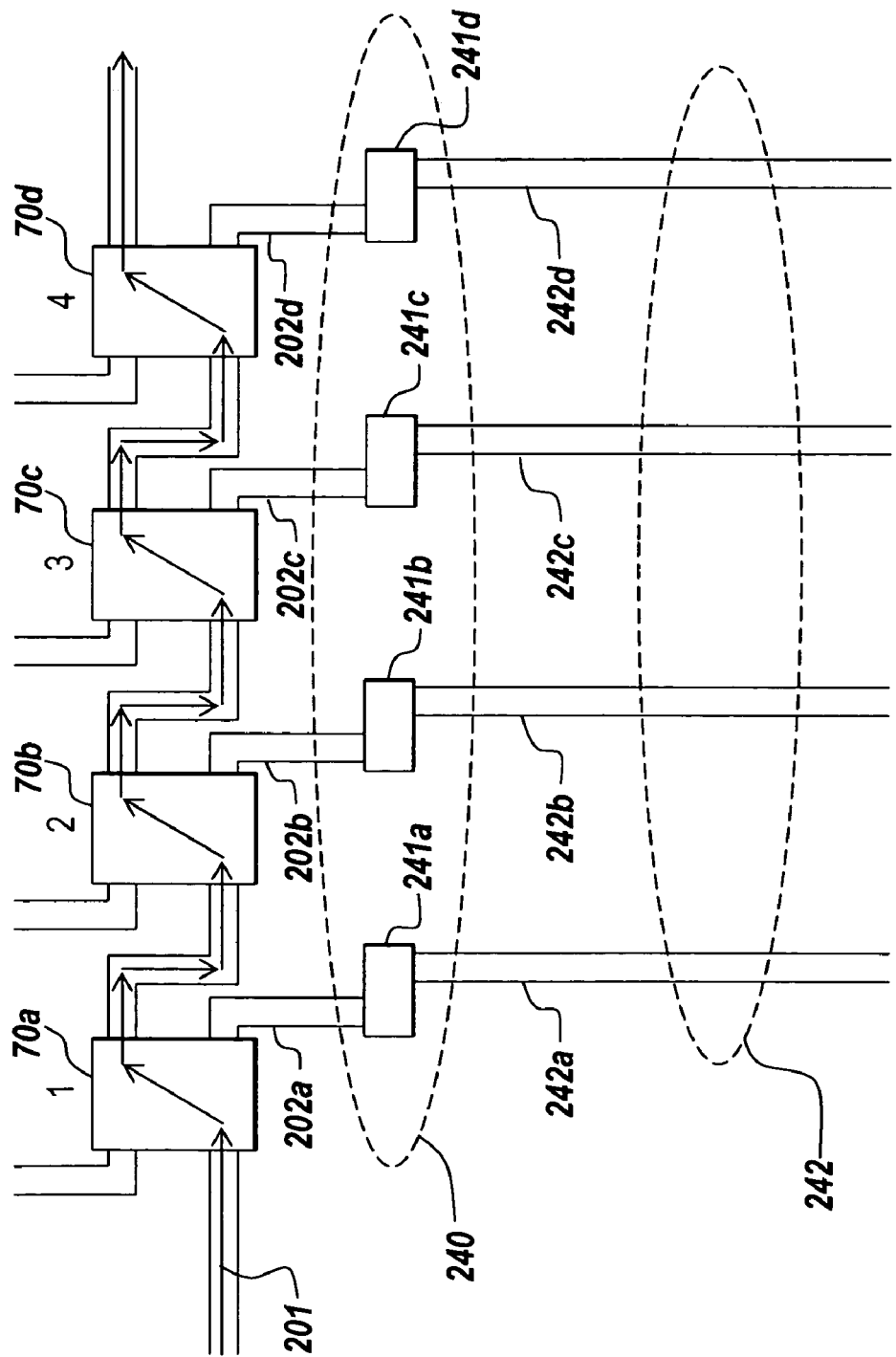
FIGS. 25A and 25B illustrates a three-dimensional sample fractionation system according to yet another embodiment of the invention.
Figure 25B:
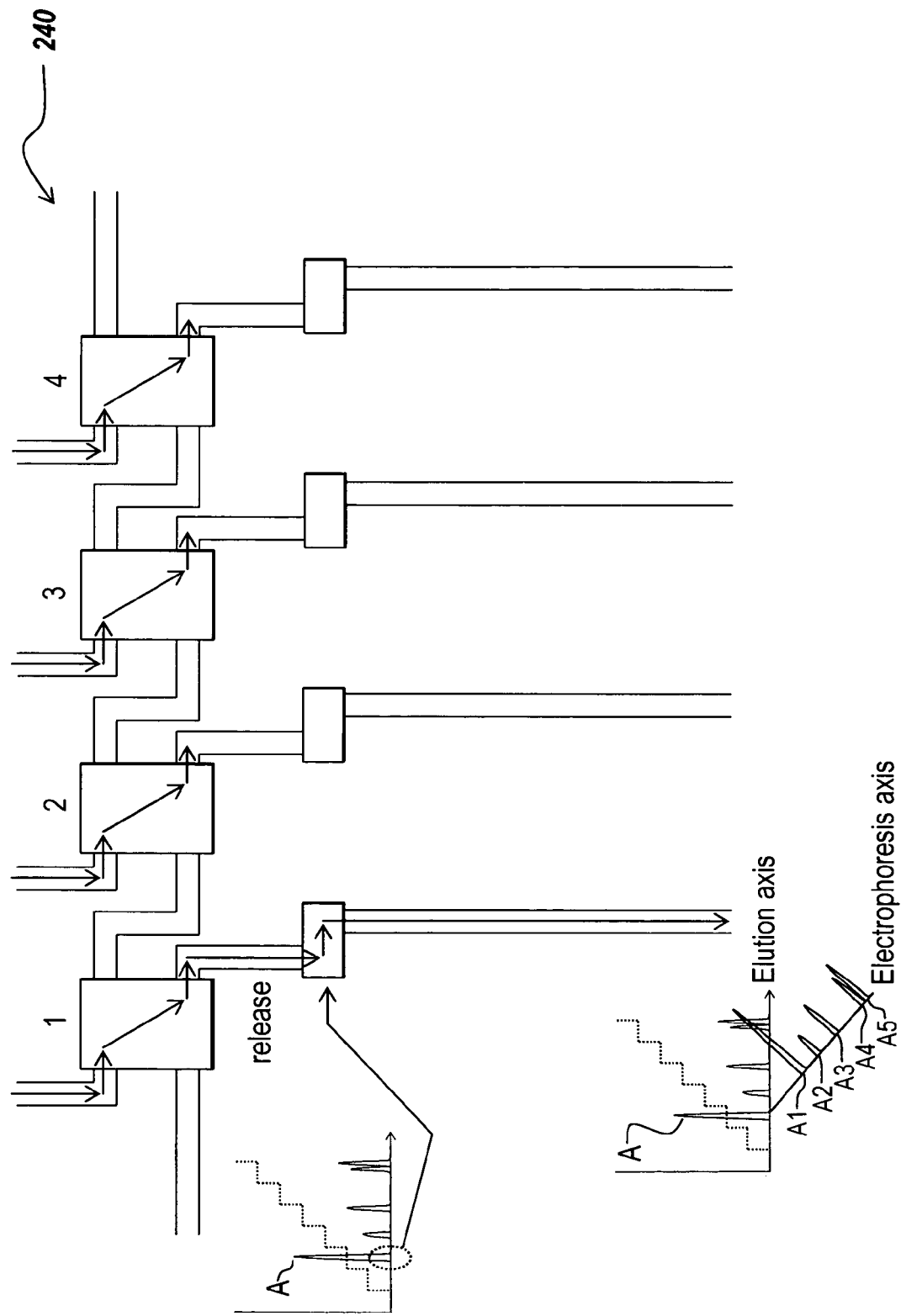

In yet another application, a plurality of affinity columns 70 may be used to form a 3-dimensional sample separation system 240, as shown in FIGS. 25A and 25B, which performs fractionation of a sample in three serial stages. The illustrative 3-dimensional sample separation system extends the two-dimensional fraction elution system described above with respect to FIGS. 24A–B, by applying electrophoretic separations to each band or sub-fraction eluted from each affinity column 70. The illustrative 3-dimensional sample separation system 240 includes a plurality of molecular fractionation devices, illustrated as an array of affinity columns 70a–70d connected in series. The system 240 fractionates a sample into a plurality of sample fractions, trapping each fraction using the matrix of an associated column, and then elutes each sample fraction into bands of different affinity, as described above. The system 240 also includes a plurality of capillary electrophoresis columns 242a–242d connected to each release channel 202a–202d of the affinity columns for separating the eluted bands from the affinity columns on the basis of size/charge or charge/mass ratio. As shown, the 3-dimensional sample separation system 240 includes a column injector 241a–241d for each electrophoretic column 242a–242d, which injects a sub-fraction or bands received from an associated affinity column into the associated electrophoretic column.

The system initializes the electrophoretic separation of each band of a sample, by first passing a sample through the sample flow path 201, such that each affinity column 70a–70d traps a selected fraction of the sample. Next, using a step gradient elution process, the trapped molecules are eluted off the affinity columns 70a–d in the form of bands of different affinity. In the illustrative embodiment, a single step of the gradient is eluted at a time and after each elution step, an aliquot from the fluid that was released from an affinity column is injected using a corresponding column injector 241a–241d into an associated electrophoretic column 242a–d and separated. Depending on the conditions in the electrophoretic column 242 (buffer, open or gel filled) the physical basis of separation may be charge, charge/mass or mass (size) or other interactions supported by a gel. The system 240 repeats the steps of eluting a sub-fraction of the sample, followed by electrophoresis of each sub-fraction released by the eluting step, until all steps of elution have been electrophoretically analyzed.

The first graph in FIG. 25B illustrates the separation of a fraction of a sample from the first affinity column into a plurality of bands. As shown, the first band A is collected and injected into the first electrophoretic column 241a, which further separates the first band A into a plurality of sub-bands A1, A2, A3, A4, A5, shown in the second graph along the electrophoresis axis.

Figure 26:
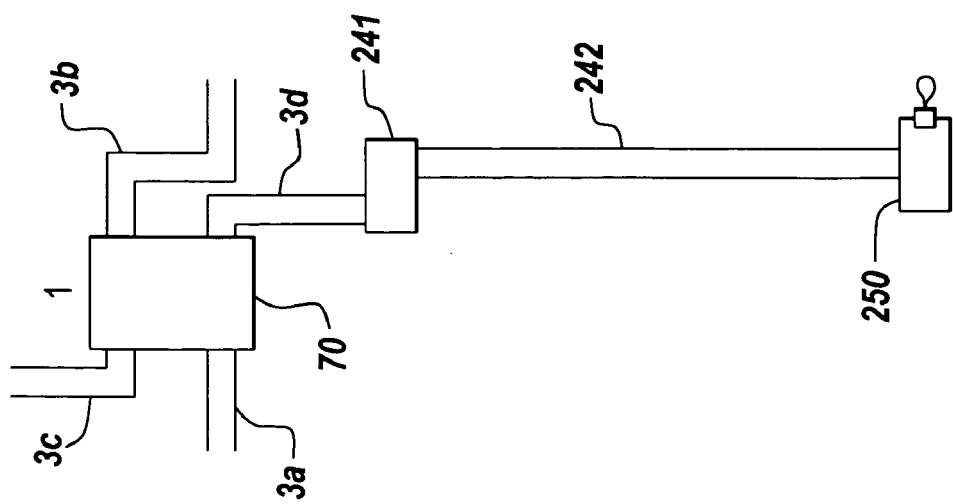
FIG. 26 illustrates molecular fractionation system including an ejection component for ejecting a sample fraction from the system.

According to another embodiment of the present invention, a component for removing or ejecting bands from a channel after separation using an electrophoresis column 242 may be included in a system implementing a molecular fractionation device according to an embodiment of the invention, such as the 3-dimensional sample separation system of FIGS. 25A–25B. For example, FIG. 26 illustrates an ejection component 250 for removing or ejecting bands from an electrophoresis column 242 after separation, suitable for introducing the ejected bands into a multiwell plate or depositing them on a MALDI—Mass spectrometer slides. The ejection component 250 can be usefully be added to the end of any of the systems described above that implement a microfluidic component, such as a molecular fractionation device for separating biomolecules.

One skilled in the art will recognize that the ejection component 250 may be placed in communication with any channel in a microfluidic system to eject a sample or a fraction of a sample from the system.

According to one embodiment, the ejection component 250 may comprise a capillary uptake pin and a virtual wall interface, or alternatively a virtual wall interface and a pressure source for droplet ejection. Suitable microfluidic ejection devices are described in U.S. patent application Ser. No. 10/028,853, filed Dec. 21, 2001, U.S. patent application Ser. No. 10/027,484, filed Dec. 21, 2001 and U.S. patent application Ser. No. 10/027,516, filed Dec. 21, 2001, the contents of which are herein incorporated by reference. One skilled in the art will recognize that any suitable component for removing a component from a channel may be used in accordance with the teachings of the present invention.

Figure 27:
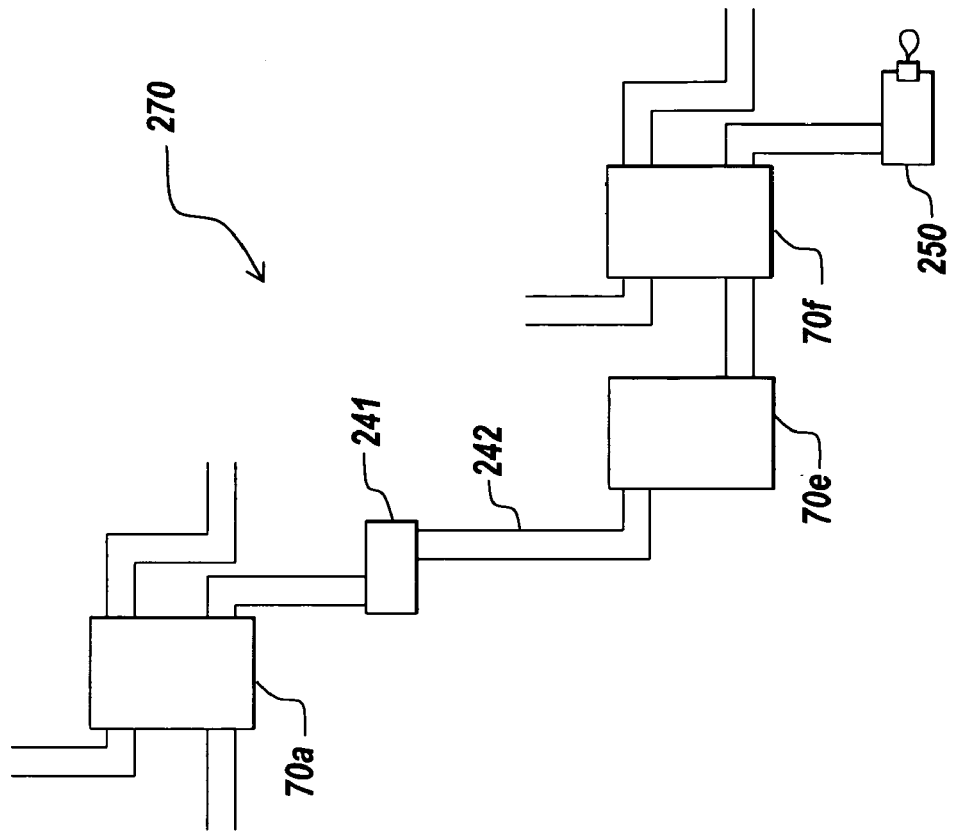
FIG. 27 illustrates a molecular fractionation system including an ejection component according to another embodiment of the invention.

Multiple molecular fractionation devices and other microfluidic components may be arranged on a chip in any suitable combination to perform a number of different applications. For example, as shown in FIG. 27, a system 270 including a plurality of molecular fractionation devices formed according to the teachings of the invention may be used to separate, digest, capture and eject a protein. The illustrative system 270 includes a first molecular fractionation device 70a, illustrated as a four-port affinity column, connected to an electrophoresis column 242 and a reactive molecular fractionation device 70e, illustrated as a two-port affinity column, coupled to the outlet of the electrophoresis column 242. The illustrative reactive molecular fractionation device 70e contains trypsin, or another suitable substance, for digesting proteins separated by a previous process using the affinity column 70a and the electrophoresis column 242. The illustrated system may also include an additional molecular fractionation device, such as a four-port affinity column 70f containing C18 reverse phase beads, or other suitable matrix, for capture of the resulting peptide digest. The system of FIG. 27 may also include an ejection component 250 to allow direct ejection of sample from the system 270 to a slide following capture of the digested peptide. The ability to digest, capture and eject a separated protein, enabled using one or more molecular fractionation devices according to the teachings of the invention, is of particular utility in subsequent use of the slides as an input to MALDI-MS with which a peptide digest of any protein can be used to uniquely identify that protein.

Figure 28:
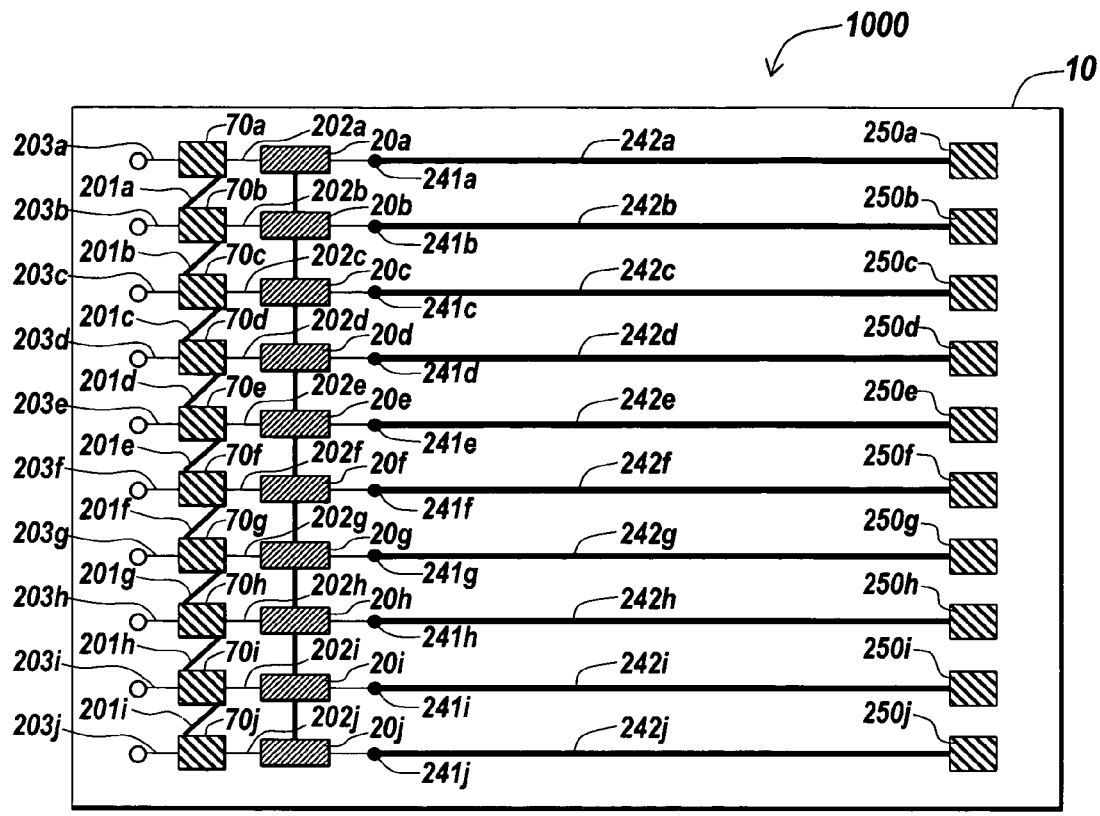
FIG. 28 illustrates a microfluidic chip suitable for protein profiling that incorporates a plurality of molecular fractionation devices and filtration systems.
Figure 29:
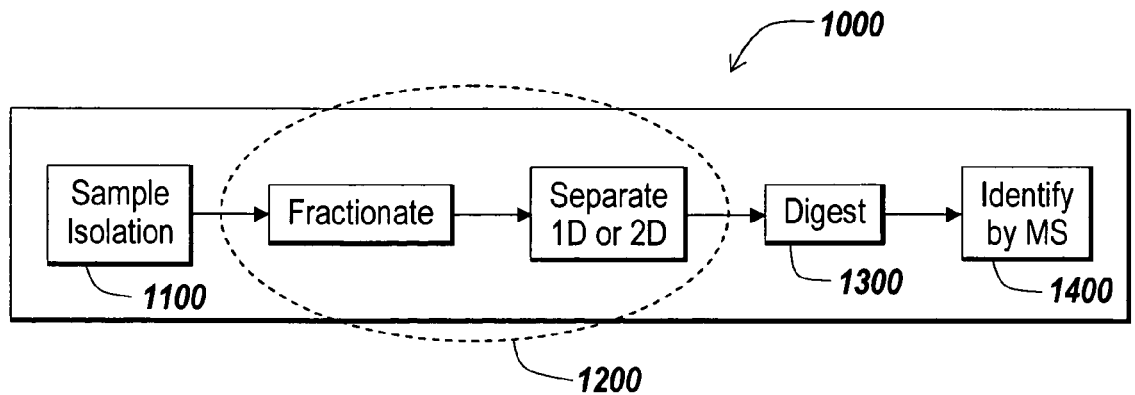
FIG. 29 is a block diagram of the chip of FIG. 28.

According to another embodiment of the invention, a plurality of microfluidic components are integrated into a microfluidic chip to integrate a plurality of microfluidic functions onto the chip. FIG. 28 illustrates a microfluidic system 1000 implementing a plurality of microfluidic components according to an illustrative embodiment of the invention. FIG. 29 is a block diagram of the microfluidic system 1000 according to an embodiment of the present invention, showing the different modules for performing a process on a sample. In an illustrative embodiment, the system 1000 may be used for protein extraction, elution, electrophoresis and dispensing. For example, the illustrative system may be used in a general protein expression analysis to selectively extract and concentrate a protein from a minimally processed sample in isolation station 1100, then fractionate the protein sample using a series of different molecular fractionation devices in fractionation station 1200. The system may then perform gradient step elutions on protein fractions bound by the affinity columns in the fractionation station 1200. The system may dialyze the elutions and separate their proteins using microchannel capillary electrophoresis (CE) separation in digestion station 1300. The system may then dispense each 5–10 nanoliter band off the CE column directly to a multiwell plate or MALDI spotting plate in identification station 1400. The use of a purification and analytical chip, such as the system 1000, interfaced with a MALDI-TOF system enables high-performance protein identification, epitope and phosphorylation mapping and protein-interaction analyses, among other applications.

The illustrative system 1000, formed on a microfluidic chip 10, includes ten molecular fractionation devices, illustrated as affinity columns 70a–70j, connected in series, each comprising a matrix selected for its affinity to selected molecules. In the illustrative embodiment, the affinity columns comprise four-port affinity columns, including a first connector port forming a sample inlet and a second connector port forming a sample outlet. The illustrative chip 1000 includes a sample input channel 2001 connected to a sample inlet of the first affinity column 70a for injecting a sample into the chip 1000 and a plurality of connecting channels 201a–201j connecting the affinity columns 70a–70j in series and forming a sample flow path 201. The chip also includes a sample outlet channel connected to the sample outlet of the last affinity column for receiving surplus sample. Each affinity column also includes a third connector port, forming an elution inlet, and a fourth connector port, forming an elution outlet. The chip further includes a plurality of elution inlet channels 203a–203j connected to the elution inlets for injecting an elution buffer to each affinity column and a plurality of release channels 202a–202j connected to the elution outlets for conveying an eluted sample from the affinity column.

A plurality of microfabricated filtration systems 20a–20j, such as any of the systems described above with respect to FIGS. 2 through 7B, are disposed in communication with the release channels 202a–202j. The filtration systems may be used to dialyze the eluted samples by resetting the buffer flowing through the release channels to prepare the eluted bands for electrophoresis. The outlets of the filtration systems are coupled to the release channels downstream to convey the dialyzed bands to an array of electrophoretic columns 242a–242j. The system also includes an array of column injectors 241a–241j connected to the array of electrophoretic columns 242a–242j for receiving and injecting eluted bands into the electrophoretic columns.

In the embodiment of FIG. 28, a sample, such as a protein sample, flows through all ten columns 70a–70j in series through the flow path 2001, defined by channel segments 201a–201j. The affinity columns fractionate the sample into ten fractions and each affinity column retains a different protein fraction. Then, the system elutes each bound proteins from the associated affinity column 70a–70j. During each elution step, the protein containing volume is dialyzed to set its buffer to an appropriate concentration for CE separation. The microfabricated filtration systems 20a–20j resets the buffer of each protein containing volume to a loading buffer. Each eluted protein fraction may then be injected, using a column injector 241a–241j, into a CE column 242a–242j for separation before being dispensed into a multiwell plate at the end of the CE column using an ejection component 250a–250j. The spacing between the columns 242a–242j at the ejector end can be well controlled to 9 mm (for 96 well plates) or 4.5 mm for 384 well plates.

A molecular fractionation system of the invention may be used with an array of different affinity columns, each selected to have an affinity for a selected protein to find members of different protein families. For example, a molecular fractionation system of an illustrative embodiment of the invention may be used to find all members of the protein families of S-100B, Creatin kinase, Myelin basic protein and Thrombomodulin in serum, and be able to separate and identify them and their variants due to post-translational-modification. These proteins have all been implicated as markers for cellular damage and indicate temporary damage to blood brain barrier.

The illustrative ejectors 250a–250j comprises a microfluidic chip component that ejects 1–10 nl volumes directly from an on chip column or microchannel. The ejector has low or no dead volume in the ejection. The ejector is placed at the end of each CE column to efficiently dispense bands into a multiwell plate or onto a MALDI surface. A suitable ejection system is described in U.S. patent application Ser. No. 10/028,853, filed Dec. 21, 2001, U.S. patent application Ser. No. 10/027,484, filed Dec. 21, 2001 and U.S. patent application Ser. No. 10/027,516, filed Dec. 21, 2001, the contents of which are herein incorporated by reference.

In the illustrative embodiment, the chip includes ten parallel systems, each comprising an affinity column, filtration system, electrophoretic column, column injector, ejector and associated channels for conveying molecules through the system. One skilled in the art will recognize that the invention is not limited to the illustrated configuration or number of components.

The system 1000 shown in FIGS. 28 and 29 provides for pre-electrophoresis sub-fractionation to simplify protein sample. For example, non-denaturing anion exchange beads can be used in an attempt to concentrate low abundance protein while enabling the functional grouping of protein. In another example, anti-phospho-tyrosine antibodies can be used for selective pre-enrichment of phosphor-tyrosine containing proteins prior to analysis by electrophoresis. Lectin beads can be used to specifically enrich glycoproteins.

The separation techniques do not destroy protein—protein interactions to allow discovery of the functions of newly discovered proteins. Such a system has an added advantage to impart additional structural characterization and elucidation of post-translational modifications, proteoglycans, carbohydrates, and unusual structures such as metalloprotein complexes by utilizing immobilized affinity separation materials.

After elution of a sample from a molecular fractionation device 70m, modifiers such as Triflouroacetic acid (TFA) can be added to the elution buffer, such that the retention of the ligand to the matrix is varied for individual sample in the crude mixture. This allows for adjustment of the selectivity of the sample by varying the modifier concentration in the buffer.

Protein in the channels may detected by covalently labeling with a florescent dye such as FITC, Fluorescamine and o-phthaldialdehyde (OPA) therefore providing label-free high throughput protein expression profiling in very small volumes. During first and second dimension separations, the labeled proteins may be monitored using a florescent detector attached to the microfluidic system. The use of fluorescent markers or other methods of detection will reveal the capturing of protein on beads. UV absorption at 280 and colorimetric stains such as SYPRO Ruby, coomassie and silver stain are other alternative ways to detect protein in channels.

For quantitative analysis of protein—sample can be labeled with one of the 3 spectrally distinct fluorescent dyes, Cyanine-2 (Cy2), Cyanine-3 (Cy3) or Cyanine-5 (Cy5). The labeling takes place via lysine residues and is carried out at stoichiometries such that only a small proportion of the protein is labeled, and is therefore compatible with in mass spectrometric analysis. Bodipy-flmaleimide can be used to covalently derivatize cysteine residues in protein.

The system of FIGS. 28 and 29 has significant advantages over current protein separation systems. For example, the system 1000 is easy to use and eliminates several laborious manual steps of sample preparation required for traditional 2D separation. The system 1000 maintains sample integrity, because the separation techniques employed do not destroy a protein and/or the protein's interaction with other components of the sample. The combination of protein separation techniques based on biochemical properties and size exclusion further avoids overlap and spears by significantly improving peak capacity. The system 100 further provides chemical programmability by allowing flexibility to design various molecular fractionation devices packed with matrices each having a specific chemistry. The system may also reduces the necessity of sample handling after loading of the complex crude sample mixture, because the peptides are eluted directly of off the molecular fractionation steps columns to the next step and finally spotted for mass spectroscopy analysis. The system further provides unbiased protein detection. For example, low abundance proteins, proteins of extreme pI and molecular weight and integral membrane proteins can be identified with the same sensitivity as other proteins. The system is also reusable, has small dead volumes with little sample loss, a reduced footprint and provides high throughput analysis. Moreover, the system 1000 enables reproducible experiments, because the protein purification by adsorption and elution utilizes biochemical and physical properties of protein and do not require acrylamide, which affects the reproducibility of an experiment A molecular fractionation system of an illustrative embodiment of the invention has several significant applications in the fields of biotechnology, and especially cytology and drug screening. Each year, more than 800,000 patients worldwide undergo myocardial procedures. Since adverse cerebral outcomes such as stroke, deterioration of intellectual function and memory deficit, occur in as many as 6.1% of such cases, the need for diagnostic strategies to reduce mortality and morbidity seems evident. Although neurological examinations and neuropsychological testing are common methods of assessing cerebral injury, these methods have the disadvantage of being expensive and time consuming. It would be of great benefit to have access to biochemical markers capable of detecting and quantifying the extent of cerebral injury. In recent past attention has been focused on the S-100B, Creatin kinase, Myelin basic protein and Thrombomodulin families of serum proteins as markers for cellular damage and indicators of temporary damage to the blood brain barrier. Enzyme linked immuno-absorbent assay (ELISA) has been used to detect and follow the level of some of these marker proteins in patient samples to show their significance. However, the ELISA assays are incapable of detecting and monitoring posttranslational modifications and relative abundance of different proteins of each family. The molecular fractionation device and system may be used to monitor in one operation all these families from serum. For example, an array of eleven affinity columns 70, listed below in the Table 1, fabricated according to an illustrative embodiment of the invention, can be used to trap, quantitate, and identify the members of all these target families of proteins from a single serum sample.

TABLE 1

| Affinity column (MFD) | Sub-fraction of Protein Family Identified | Disease Implication |
|---|---|---|
| S100β Antibody | S100β | Marker for extend of brain injury caused by cerebral ischemia and cerebral fungal infection |
| Calmodulin | S100 | |
| IMAC | S100 | |
| Interleukin-6 (IL-6)-Antibody | interleukin-6 (IL-6) | Proinflammatory cytokines play an eminent role in pathophysiology of infection and inflammation |
| tumor necrosis factor-alpha (TNF-alpha)-Antibody | tumor necrosis factor-alpha (TNF-alpha) | |
| interleukin-1beta (IL-1beta)-Antibody | interleukin-1beta (IL-1beta) | |
| C-Reactive protein-Antibody | C-Reactive protein | |
| Concanavaline A | Cytokines | |
| Thrombomodulin-Antibody | Thrombomodulin | Varying degree posttranslational modifications of O- and N-glycosylations |
| Ricinus cummunis agglutinin I | Neuron-specific enolase | There are many different posttranslational modifications including N- and O-glycosylation at multiple sites, sulfation, phosphorylation, hydroxylation and numerous gamma-carboxyglutamic acids associated with protein function |
| Gelatin | Metalloproteinase 9 | Elevated levels associated with disease state |

A microfluidic component, such as a molecular fractionation device, integrated to a microfluidic system using a capping module in accordance with the teachings of the present invention provides significant advantages. The device is externally manufacturable and fillable and then assembled onto the glass chip. The invention allows an array of affinity columns or other microfluidic elements to be each connected to capillary electrophoresis system. The system may be customized by a user according to his or her particular needs. For example, a user may able to request a cartridge with ten affinity columns of their own choice, followed by automated assembly of pre-stocked columns onto pre-stocked plates and shipment. Many versions of the molecular fractionation system can be customized for any suitable application.

A specific selection and order of affinity columns along with the elution buffers and reagents and step pattern represents the "program" of the cartridge. A user lab may set up its program for a useful proteomics "fingerprint" and allow collaborating groups to use it. This customization concept provides a natural path for research in proteomics fingerprints for disease to migrate into clinical use. This is in contrast to the situation with 2DE proteomics in which there is no simple transition into clinical use do to reliability and complexity.

Figure 30:
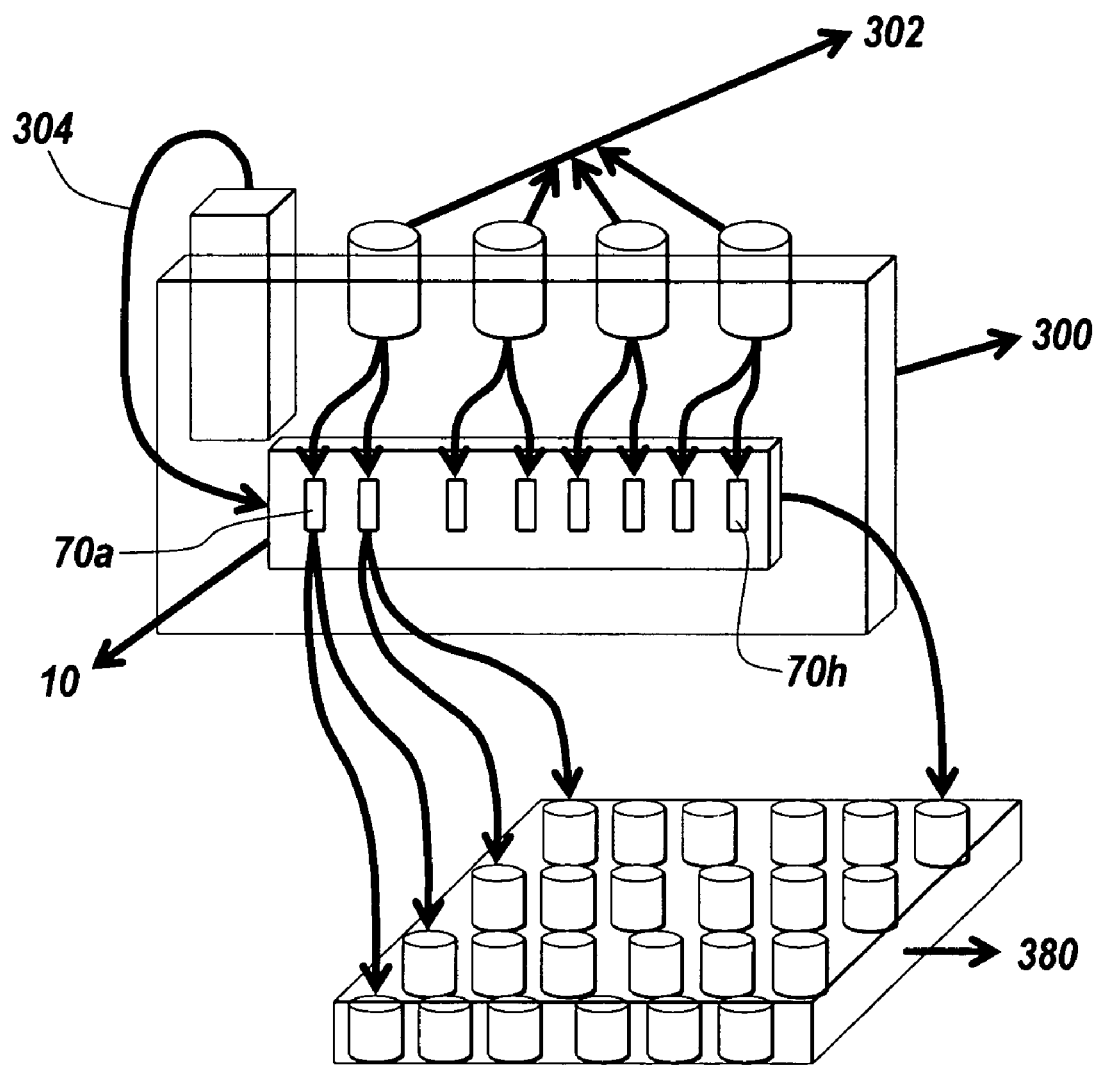
FIG. 30 illustrates a: single channel system with microscale affinity and dialysis unit integrated on the same chip using the teachings of the present invention

FIG. 30 illustrates a multidimensional programmable affinity fractionation (MPAF) system 300 for protein identification, extraction, elution and dispensing. The MPAF system 300 incorporates a plurality of molecular fractionation devices, such as the affinity columns 70 described above, that separate proteins using biochemical molecular criteria in addition to physical properties such as molecular weight and isoelectric focusing. Affinity fractionation using the affinity columns of the present invention provides an additional dimension that enables distinguishing between molecules whose amino acid sequences are identical but which differ in expression levels and post-translational modifications and hence functionality.

FIG. 30 illustrates a single channel MPAF system 300 with a plurality of affinity columns 70a–70h forming microscale affinity and dialysis units integrated on the same chip 10 using capping modules filled with a selected matrix. The illustrated MPAF system 300 is an automated, microfluidic, multiplexed and multidimensional fractionation-based proteome analysis system. Affinity columns, bead precipitation steps and/or selective labeling of protein samples are used to isolate sub fractions and selectively capture, elute and dispense fractions of proteins from complex protein samples. The matrix in the affinity columns can comprise any affinity beads with any chemistry including antibodies, small and large molecule ligands, molecular "baits" and transport molecules (such as albumin). Proteins from fractionated sub-proteomes are provided from a supply source 304 and separated by capture and elution using affinity columns 70a–h, as described above. The captures fractions are selectively eluted from each affinity column 70a–h based upon their affinity profiles and the binding efficiencies of various components. The captured fractions are eluted from the matrix 78 of each affinity column 70a–70h using a step or continuous gradient of elution buffer from elution buffer supplies 302. These separated fractions from various molecular fractionation units can be dispensed in wells of a micro well plate 380 or directly spotted for capillary electrophoresis, 2D electrophoresis or mass spectroscopy analysis. Separated fractions can be monitored by any combination of methods based on fluorescence, bioluminescence, chemiluminescence, mass spectrometry, radioactivity or electrochemistry.

Multidimensional protein identification can be achieved in the system 300 of FIG. 30 by designing and organizing the affinity columns 70*a*–70*h* in either linear or tree arrays or a combination of both of these schemes.

For example, in a linear multidimensional programmable array, such as the array shown in FIGS. 23A–25B, each affinity columns can be programmed for different chemistry and arranged based upon experimental need. The multidimensionality of the system is a function of number of affinity columns 70 and number of elution steps. In a linear array, each affinity column is arranged in series, such that only the flow through from the preceding affinity column is loaded onto the secondary affinity column. As the sample flows through the first affinity column, specific proteins are captured based on the affinity chemistry of the initial affinity column. The arrangement of affinity column in this scheme allows for both qualitative and quantitative information about separated fractions. For example, all proteins with phosphotyrosine could be retained in the first unit while the flow through from this unit with phosphoserine and phosphothreonines and unphosphorylated proteins can be captured by the subsequent affinity columns. Sample load for subsequent affinity columns will not have protein samples with phosphotyrosine. Captured molecules from each MFU are subsequently eluted by a step gradient of elution buffer. These separated fractions can be used for further analysis by conventional means. The linear array can be used to study the proteins involved in pathway analysis since each affinity column can be used to capture and separate interacting proteins.

Figure 31:
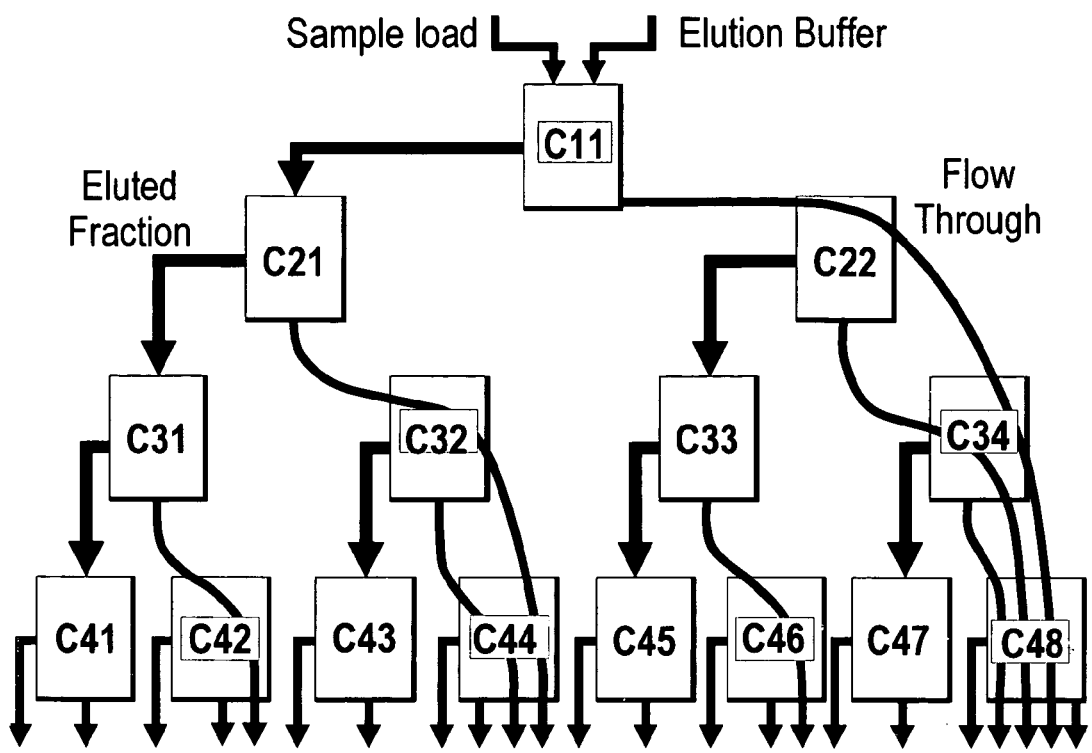
FIG. 31 is a schematic drawing of a tree array arrangement of a plurality of molecular fractionation devices.

FIG. 31 is an example of a tree array arrangement of affinity columns for multidimensional programmable affinity fractionation. As shown, a plurality of molecular fractionation units, illustrated as affinity columns 70, can be arranged in a "tree" configuration. Both the flow through and the eluant from a preceding affinity column is loaded onto two separate and subsequent affinity columns having the same affinity chemistry. Sample in binding buffer is loaded on to a first column at position 1 (C11). Flow through from this column is loaded onto the second column at position 2 (C22) and an elution fraction is loaded onto the second column at position (C21). A flow through fraction from C21 has molecules that have affinity for beads in C11 but do not bind to C21. Elution fraction from C21 has affinity for both C11 and C21 columns. A microdialysis unit may be implemented between different eluant loading steps but not for loading samples from flow through. Such a configuration can be used to study overlapping classes of proteins (combinatorial analysis of protein affinity), such as proteases that are glycosylated and phosphorylated. Captured molecules from each affinity column can be eluted by a step gradient of elution buffer. Such an arrangement of affinity columns may be preferred for combinatorial qualitative analysis of protein expression for a given proteome. Separated fractions can be used for further analysis by other conventional technologies.

The MPAF system 300 has significant advantages for fractionation and separation of proteins and other substances. For example, the described technology supports multidimensional separation on a single chip by using different affinity units and multiple elution steps to elute captured molecules. Identification and separation of proteins by affinity binding provides additional dimensions that include information about functional and conformational criteria to identify those whose amino acid sequences may be identical but which differ in post-translational modifications and functionality.

The MPAF system 300 is also programmable. An experimental design can be selected to support a wide variety of commercially available and/or specially designed affinity beads. The arrangement of numerous affinity columns on a single chip provides an easy method of encoding the system for a desired protein study. This provides for both qualitative and quantitative analysis, simultaneously.

The MPAF system 300 can also be easily and rapidly deployed and can enhance the ability to detect specific diseases and accelerate the time required to identify a disease outbreak. The system 300 is an easily deployable diagnostic tool using protein activity profiles to identify specific disease states. Affinity columns, formed using capping modules and a selected matrix, can be quickly deployed (within 48 hours) in response to new clinical assay requirements (e.g. for detection of bioterrorism agents).

The MPAF system 300 is also compatible with automation. For example, robots can be used for filling, assembling and placing micro-affinity units, such as affinity columns 70, on glass chips with appropriate fluidic networks. This lends itself to standardized manufacturing and low cost production.

The design is cost effective both in terms of time and price. The cost and time required to design, fabricate and fill chips with desired affinity bead chemistries is lower than using standard microfluidic channels. The cost of the technology is also competitive with existing proteomics techniques.

Furthermore, the molecular fractionation devices implemented using a capping module according to the teachings of the invention use commercially available affinity beads, which can be reused. A glass chip can also be reused with a different set of pre-assembled microfluidic elements placed on the chip by pick and place assembly equipment.

Moreover, by fractionating samples in a sub-proteome, protein separation problems can be reduced from separating thousands of proteins to less than a hundred proteins. This further facilitates sample handling for subsequent analysis of fractionated sample, which allows for an increased ability to load proteins for CE electrophoresis, removal of a large quantity of masking proteins, reduced sample complexity, which enables use of 1DE methodologies instead of 2DGE methodologies. The system further provides a better ability to handle large protein complexes (above 100 kDa), a better ability to handle extreme pI and hydrophobic proteins, better quantization and increased reliability and consistency from run-to-run.

The MPAF technology can be easily combined with and integrated into existing techniques (e.g. 2DGE, MS) and any other protein assays such as ELISA, cell based assays and others for activity, binding and functionality.

Multidimensional programmable affinity fractionation technology can be used for both qualitative (e.g. type of post translational modification) and quantitative (degree of post translation modification) information and therefore functional and structural information about the proteins. Some examples of the types of issues that can be addressed by the technology include:

Post-translational modification (PTM): The affinity chromatography procedures of the present invention can isolate post translated proteins and their states from unmodified proteins. A single step through a molecular fractionation device replaces multiple complex procedures required using 2DGE or other techniques. For example, a set of phosphorylated proteins can be isolated by capturing modified proteins on anti-phophotyrosine and/or anti-phosphothreonine/phosphoserine antibody affinity beads (e.g. from Qiagen) while unphosphorylated proteins are recovered in the flow-through fraction. Such sub fractions greatly reduce proteome complexity and greatly facilitate phosphorylation-profile studies. Both fractions retain full biological activity and can be further purified if desired. Phosphorylation modulated signals in those samples can be identified by comparing the fractionated protein samples across different experiments using the multidimensional programmable affinity fractionation technology of the present invention.

Activity-Based Protein Profiling (ABPP): By employing probes immobilized on beads that covalently link to an enzymatically active site fraction, one can identify and isolate "active" enzyme families Such affinity protocols have been used to isolate active fractions of proteins from inactive or denatured mixtures. MPAF provides an implementation of this same technology in a microfluidic format using much lower sample volumes.

Protein—Protein interaction: Protein-protein and protein-ligand interactions can be studied, by activating beads with "bait" molecules and isolating the fractions of proteins that bind to the "bait". This approach is routinely used by many groups to study protein—protein interactions. The same class of experiments can be done using MPAF technology to study and extract molecules interacting with a protein of interest or identify molecules interacting in specific signaling or metabolic pathways.

Sub-Proteome Elution: On a single cartridge/chip, the technology described herein can capture fractions from whole cell/tissue extracts with complete proteomes and subsequently elute them into sub-proteomes for further analysis. This avoids sample preprocessing required using existing techniques.

Sample enrichment: The present invention allows for sample enrichment using affinity capture and elution of low abundant proteins. This can be done in one of the two ways (i) by eliminating masking proteins or (ii) by capturing molecules of interest from a large volume of sample but eluting those using smaller volumes of elution buffer. This eliminates multiple steps required by conventional techniques.

Exemplification of the Invention

EXAMPLE 1

A plurality microfiltration devices with fluid channels, such as one of the devices shown in FIGS. 2–7B, were assembled on a chip. The microfiltration devices had a capacity of between about 1–2 µl to demonstrate the ability to set and reset buffers and small molecule concentrations in a flow stream containing proteins.

Figure 32:
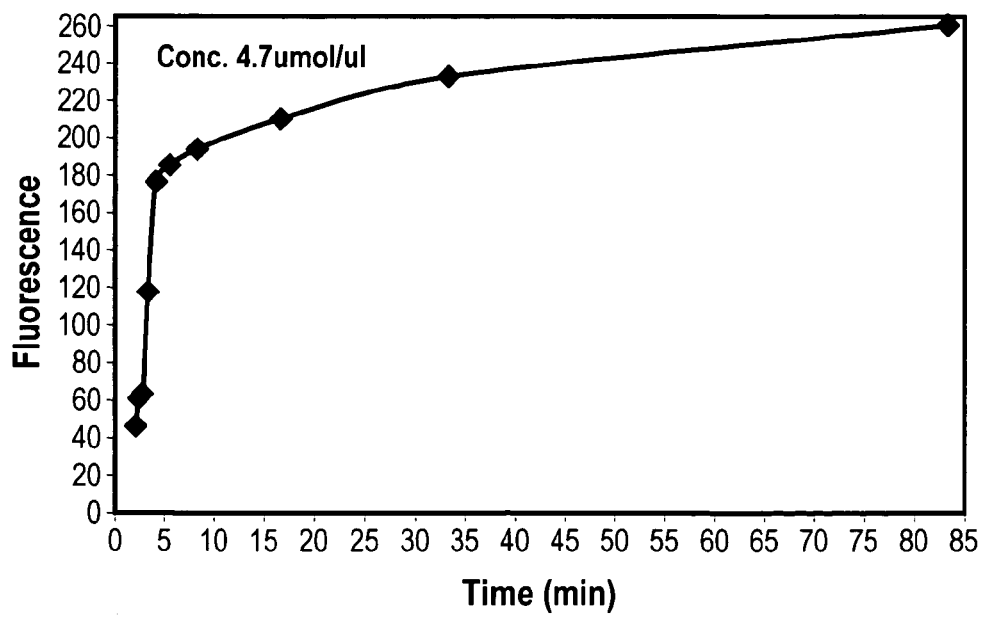
FIG. 32 illustrate experimental results showing the Fluorescence spectra for Fluorescein salt from the flow through collected from a microfiltration device.

To demonstrate the diffusion of small molecules across the filter membranes of the microfiltration devices a mixture of 0.1 mM Fluorescein sodium salt (Sigma catalog #F6377) and 0.01 mM Rhodamine labeled BSA (Sigma catalog #A2289) in a phosphate buffered saline (PBS) pH 7.2 was passed through the channel on one side of each membrane and an accumulation of small molecules was detected on the other side. Flow through from the experimental step was monitored by collecting samples in micro well plates and recording excitation and emission spectra at 485 and 518 nm for Fluorescein sodium and at 544 and 590 nm for Rhodamine labeled BSA (RBSA). These results are shown in FIG. 32. The graph in FIG. 32 shows the Fluorescence spectra for Fluorescein salt from the flow through collected from the capping module of the microfiltration device. The amount of fluorescence observed is related to the amount of Fluorescein sodium salt present in the sample that has diffused from the glass channel through the dialysis membrane in the capping module channel.

As expected, the amount of small molecules diffused through the membrane is dependent upon the initial amount present. Larger molecules (Rhodamine labeled BSA) are retained through the filter membrane. The amount of small molecules recovered across the membrane increased with an increase in the dialysis time (i.e. time flow is resident on the dialysis membrane).

EXAMPLE 2

Glass chips with appropriate plumbing were designed and fabricated. To fabricate a fluidic circuit, channels in the glass chips were manufactured by chip microfabrication. The channels or plumbing were fabricated by etching channels in a glass plate followed by bonding of a second glass plate to enclose the channels, forming sealed microchannels. Vertical communication ports were laser machined in the glass to connect the channel to an exterior surface of the glass chip.

Capping modules were formed comprising plastic structures having a 3×5 mm planar cross section with a 6×0.04×1 mm channel formed in the base on the side that will be mounted towards the glass. The capping modules were prepared in arrays of 3×3 caps. Molecular fractionation devices were built by starting with a capping module array and sequentially bonding the following: a polyester bonding layer, a filter membrane layer, and another polyester bonding layer in a batch process to makes nine (a 3×3 array) molecular fractionation devices at a time. 25 mm wide polyester films were laser cut to place 500-micron holes in precise positions for the fluid path (i.e. aligned to the channel in the cap and the communication ports in the glass chip). High strength 3M acrylic glue (9471LE Adhesive transfer tape) was laminated on a both sides of the patterned polyester films to make 125 micron thick "polyester bonding layers". Whatman 47 mm diameter Nucleopore track-etch 2 micron filter membranes were used (catalogue # F0247) as the filter membrane.

After batch fabrication, the molecular fractionation devices were individually mounted on one or more glass chips. When fully assembled, the holes in the two polyester layers were aligned with the ports on the glass chip and column structure in the capping module to allow fluid flow from the chip through the filter into the capping module, then over the matrix in the capping module and back out to the chip through the filter. Each four-port molecular fractionation system included two flow paths: a first fluid path for flowing samples through the membrane over the matrix and out through the membrane again and a second, similarly formed, fluid path for sample elution. The elution path was designed to start before and end after the sample-loading path to ensure that the sample coat is thoroughly rinsed with elution buffer.

A mixture of CD7 FITC labeled antibody (mouse IgG2a subclass) and CD33 RPE labeled antibody (mouse IgG1 subclass) was purchased from Exalpha (catalogue # B733). After a molecular fractionation device was attached to the glass chip with appropriate plumbing, protein A agarose beads (Pierce catalogue # 53142) were loaded into the capping module. The capping modules were filled with 60% protein A beads in binding buffer by injecting 5 μl from a loading port. The loading port was then sealed with a polyester film coated with adhesive.

Antibody mixture was loaded on to the protein A beads in a binding buffer (1.5M Glycine/NaOH, 3M NaCl, pH 9.0) and eluted off into sub fractions by step gradient of an elution buffer (0.1M Sodium Citrate, pH 5.5). Various proportions of binding and elution buffers were mixed to make different steps of elution buffer gradient. All the chemicals required for various buffers were bought from Sigma Aldrich.

Sample was loaded on the protein A agarose beads by flowing antibody mixture in binding buffer from one flow path while the other flow path was closed by valves. Next, the column was washed with twenty times the column volume (5 ul) of binding buffer (i.e. 100 μl) which removed non-specifically bound molecules. This step was followed by ten steps of an elution buffer wash. In every other step of the elution buffer wash, the concentration of the elution buffer was increased by 20%. Flow through from each experimental step was monitored by collecting samples in micro well plates and recording excitation and emission spectra at 485 and 518 nm for FITC labeled antibodies and at 544 and 590 nm for RPE labeled antibodies.

EXAMPLE 2A

In a first example, the molecular fractionation device was preloaded with sample, followed by sub fraction elution using step gradient of elution buffer.

In the first example, the capping modules were prepared with matrix preloaded with sample. Protein A agarose beads were washed with ten times the volume of beads. A 1:1 ratio of antibody mixture and binding buffer was added to the prepared beads. 5 pt of this mixture was then loaded in the capping modules on the chips. As described above, there are two steps involved in the elution of sub fractions of samples. In a first step, the molecular fractionation device was washed with twenty times the volume of the capping module with a binding buffer to remove non specific binding by flowing binding buffer over the beads. In a second step, elution buffer with increasing concentration of elution buffer was used to elute sub fractions of trapped antibodies. Ten steps of concentration gradients were used with 20% increase in the elution buffer in every other step.

Figure 33:
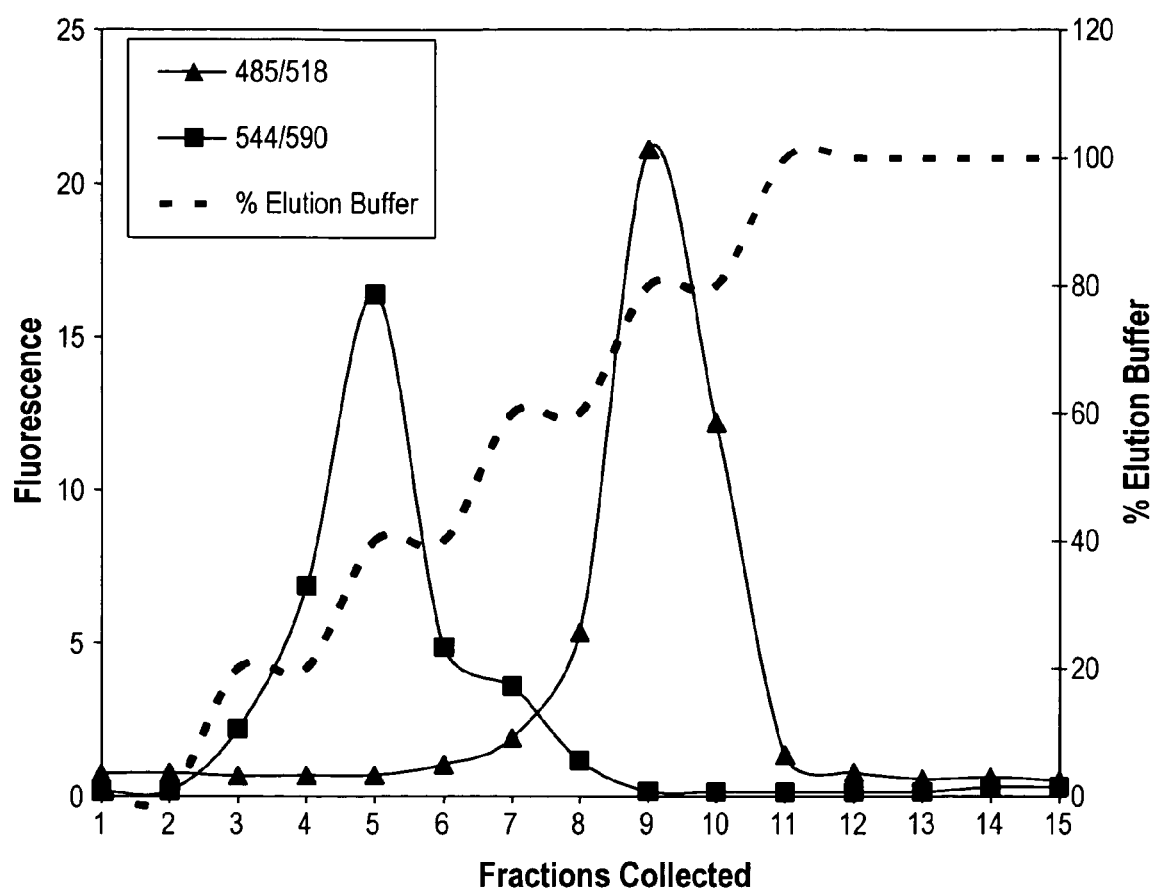
FIG. 33 illustrates elution results from a first experiment using a molecular fractionation device of an illustrative embodiment of the invention.

Flow through from each experimental steps described in previous section was monitored by collecting samples in micro well plates. A Fluoroskan ascent FL multiwell plate reader from Thermo Labsystems was used to monitor excitation and emission at 2 wavelengths simultaneously; excitation and emission spectra at 485 and 518 nm for FITC labeled antibodies and at 544 and 590 nm for RPE labeled antibodies. The results of the monitoring are plotted in FIG. 33. FIG. 33 illustrates the resolution of different sub fractions of molecules captured on the Protein A beads in the cap when eluted with step elution. Antibodies labeled with RPE belong to the mouse IgG2a subclass of antibody has lower binding affinity to the Protein A compare to FITC labeled mouse IgG1 subclass. As these results indicate RPE labeled (544/590 excitation/emission spectra) antibodies elutes before FITC labeled antibodies (485/518 excitation/emission spectra). These results clearly demonstrate the elution of sub fractions of sample from the preloaded molecular fractionation device with varying the elution buffer concentration by step gradient.

EXAMPLE 2B

In a second example, the sample was loaded onto the molecular fractionation device in situ, followed by step gradient elution.

In the second example, a 400 μl volume 1:1 mixture of two different subclasses of antibodies in binding buffer was loaded on the matrix of a molecular fractionation device with protein A in the capping module by flowing the sample over the beads (matrix). Three steps were involved in this experiment. In a first step, the "molecule capture step", specific antibodies from the sample were trapped as the sample flowed through the membrane, over the beads, and out through the membrane. While the sample was loaded on the beads, the second flow path was closed. Four steps of 100 μl of the sample were used to load the sample. In the second step, the "weak/non specific binding wash", the molecular fractionation device was washed with 200 μl of binding buffer to remove non specific binding by flowing binding buffer over the beads. In the third step, the "elution step", ten steps of five different elution buffer concentrations were used to elute sub fractions of trapped molecules.

Figure 34:
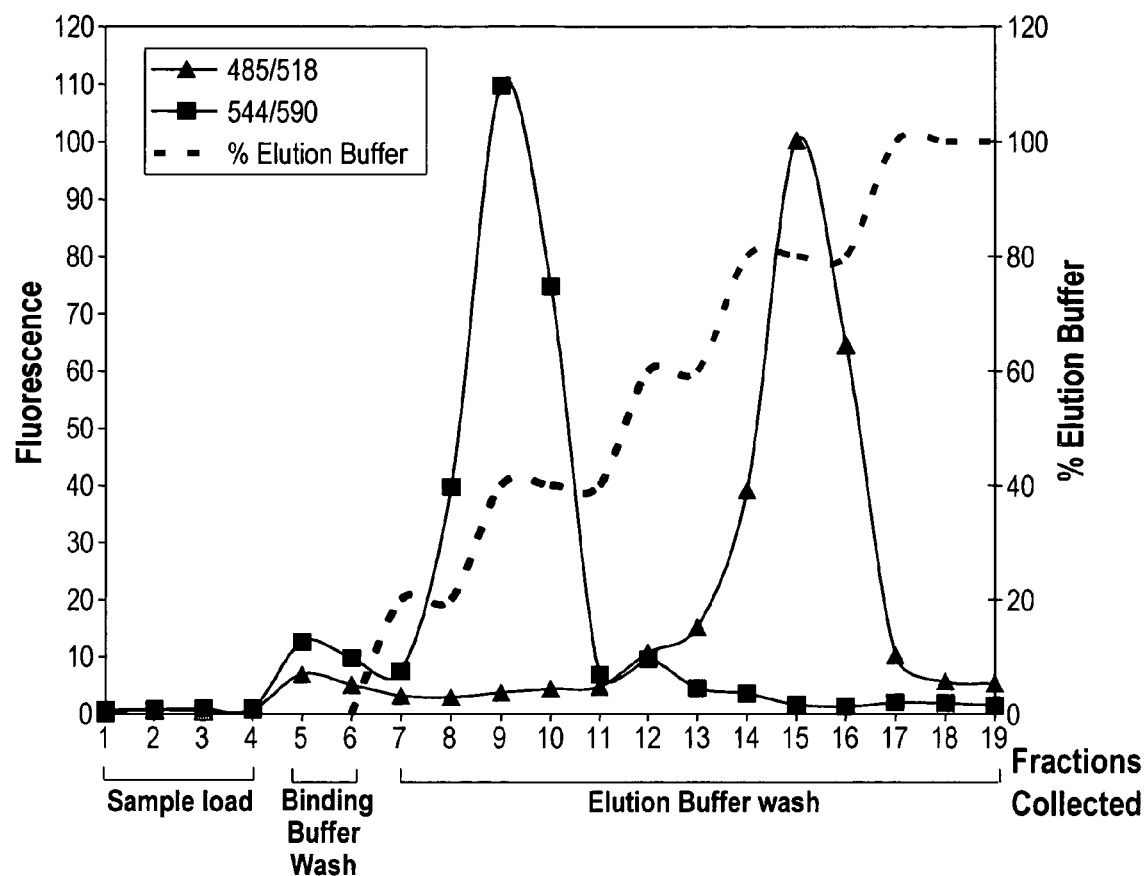
FIG. 34 illustrates elution results from a second experiment using a molecular fractionation device of an illustrative embodiment of the invention.

Flow through from each experimental step in the second example was monitored by collecting samples in micro well plates. A Fluoroskan ascent FL multiwell plate reader from Thermo Labsystems was used to monitor excitation and emission at 2 wavelengths simultaneously; excitation and emission spectra at 485 and 518 nm for FITC labeled antibodies and at 544 and 590 nm for RPE labeled antibodies. The results of the monitoring step are plotted in FIG. 34. FIG. 34 demonstrates the use of a microfluidic system with a capping module structure with affinity matrix with specific binding sites to capture molecules. Fractions 1–4 were collected as flow through for the sample load during the molecule capture step (Step 1). Results for step 2, binding buffer wash are in fraction 5 and 6. Fractions 7–19 were collected during the step 3 of the experiment. In this step, molecules were eluted as sub fractions using step gradient of elution buffer. Mouse IgG2a subclass of antibody (labeled with RPE) has lower binding affinity to the Protein A compare to mouse IgG1 subclass (FITC labeled). As these results indicate, RPE labeled (544/590 excitation/emission spectra) antibodies elutes before FITC labeled antibodies (485/518 excitation/emission spectra).

As seen in the results, plotted low fluorescence observed in the sample load steps indicate capture of antibodies by the protein A on the beads. Capture efficiency of the beads in the affinity column is better than 98%. Antibodies retained on the protein A column were subsequently eluted by varying the elution buffer concentration by step gradient. More than 93% of the sample was recovered and 71% was in the major peak for both sub classes of antibodies.

EXAMPLE 2C

In a third experiment, a sample was loaded onto a molecular fractionation device in situ, followed by step gradient elution with 7.5×–9.5× concentration enrichment.

In the third example, one ml of 1:100 ratio of a mixture of two different subclasses of antibodies to binding buffer was loaded on the matrix of a molecular fractionation device with protein A in the capping module by flowing the sample over the beads. The third experiment also involved three steps. In a first step, the "molecule capture step", specific molecules from the sample were trapped on the affinity column matrix as the sample flowed through the membrane, over the beads, and out through the membrane. The second flow path was closed while the sample was loaded on the beads. In a second step, the molecular fractionation device was washed with binding buffer to remove non specific binding by flowing binding buffer over the beads. In a third step, the elution step, a flow through step gradient of elution buffer was used to elute sub fractions of trapped molecules from the matrix of the molecular fractionation device.

Figure 35:
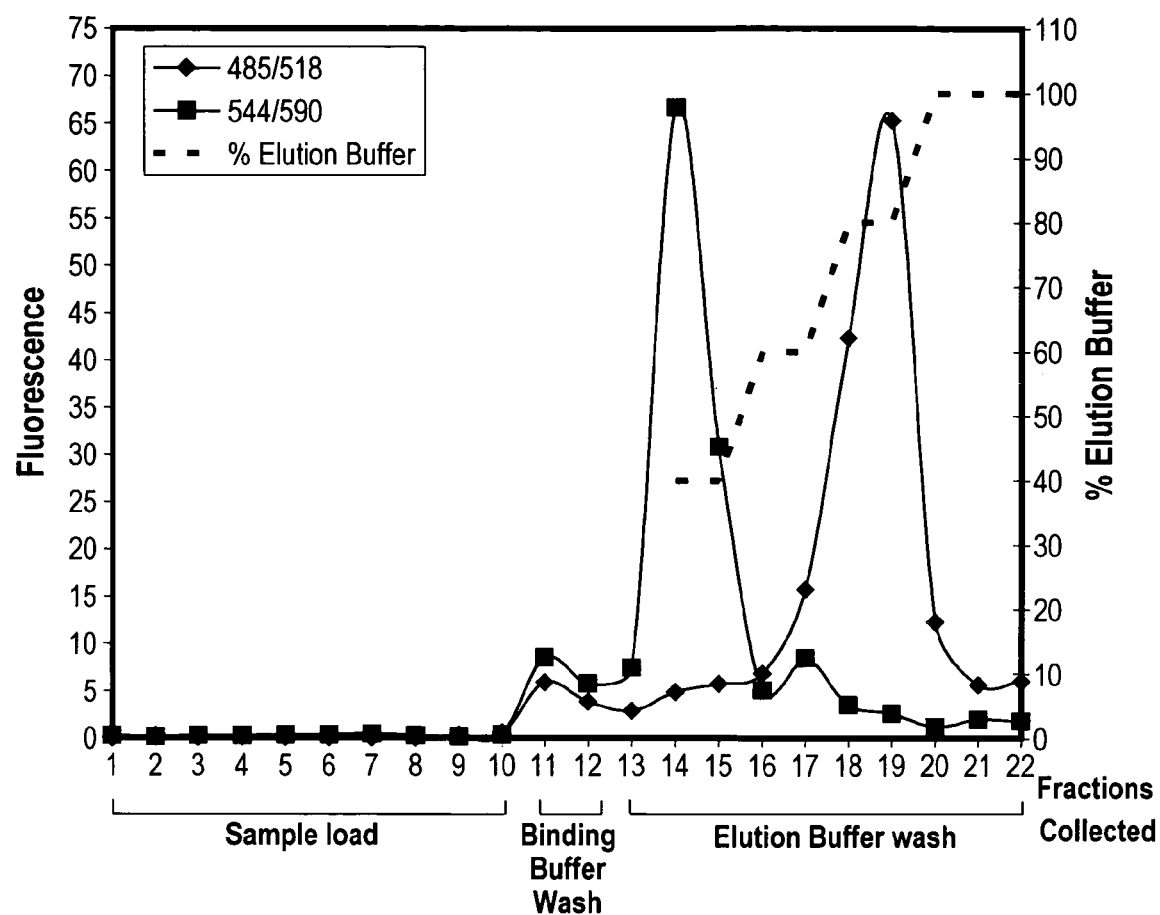
FIG. 35 illustrates elution results from a third experiment using a molecular fractionation device of an illustrative embodiment of the invention.

Flow through from each experimental step in the third experiment was monitored by collecting samples in micro well plates. A Fluoroskan ascent FL multiwell plate reader from Thermo Labsystems was used to monitor excitation and emission at 2 wavelengths simultaneously. For FITC labeled antibodies, excitation and emission spectra at 485 and 518 nm was used and for RPE labeled antibodies, excitation and emission spectra at 544 and 590 nm was used. The monitoring results for the third experiment are plotted in FIG. 35. FIG. 35 demonstrates the use of microfluidic system with a cap structure with affinity matrix with specific binding sites to capture molecules. Fractions 1–10 were collected for the sample load step (Step 1). As seen in FIG. 35, the results plotted low fluorescence observed in the sample load steps indicate capture of antibodies by the protein A on the beads from a dilute antibody solution. Capture efficiency of the beads in column was better than 98%. Results from the second step, the binding buffer wash, are in fractions 11 and 12. Fractions 13–22 were collected during the third step of the third experiment. In the third step, molecules were eluted as sub fractions using a step gradient of elution buffer. These results demonstrate the use of this embodiment of a molecular fractionation device. Briefly, IgG2a and IgG1 molecules in solution flowed over the trapped beads containing protein A molecules. Since IgG2a has a lower binding affinity to protein A than IgG1 the IgG2a eluted off at a lower concentration of the elution buffer. Mouse IgG2a subclass of antibody (labeled with RPE) has lower binding affinity to the Protein A compared to mouse IgG1 subclass (FITC labeled). As these results indicate, RPE labeled (544/590 excitation/emission spectra) antibodies elute before FITC labeled antibodies (485/518 excitation/emission spectra). For antibody labeled with RPE and antibodies labeled with FITC we get 79% and 77% respectively of the sample elutes in each four fraction wide peak and we achieve peak concentration enrichment of 9.5× and 7.5× respectively at the maximum single fractions.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A microfluidic system, comprising:
a first microchannel formed in a substrate;
a first communication port coupling the first microchannel to a surface of the substrate; and
a capping module forming a chamber and having a matrix having an affinity for selected molecules disposed in the chamber and a trapping filter forming a sidewall of the chamber for compartmentalizing the matrix on the capping module, wherein the trapping filter includes a semipermeable membrane that is permeable to fluids and impermeable to the matrix, wherein the capping module is adapted to be stacked on the substrate and placed in communication with the first microchannel, the capping module further comprising a first connector port extending through the semipermeable membrane for placing the chamber in fluid communication with the first communication port, and a second connector port extending through the semipermeable membrane for connecting the chamber in fluid communication with a second communication port that couples a second microchannel to a surface of the substrate, thereby forming a fluid path between the first microchannel and the second microchannel.

2. The system of claim 1, wherein the matrix comprises an array of affinity beads for selectively binding to the selected molecule.

3. The system of claim 2, wherein the affinity beads are coated with binding sites configured to bind to the selected molecules.

4. The system of claim 1, wherein the matrix includes an enzyme for reacting with the selected molecules.

5. The system of claim 1, wherein the matrix includes detection molecules that react with a sample to produce a measurable reaction.

6. The system of claim 1, further comprising a capillary electrophoresis column coupled to the second microchannel.

7. The system of claim 1, further comprising an impermeable layer covering the semipermeable membrane, wherein the impermeable layer does not cover the first and second connector port to allow liquid flow through the first and second connector port.

8. A capping module for a microfluidic system, comprising:
a substrate forming a recess;
a matrix disposed in the recess on the substrate, the matrix having an affinity for selected molecules,
a trapping filter, including a semipermeable membrane, covering the recess to form a chamber for compartmentalizing the matrix on the substrates,
a first connector port extending through the semipermeable membrane for placing the chamber in communication with a first microchannel,
a second connector port for placing the chamber in communication with a second microchannel,
a third connector port for placing the chamber in communication with a third microchannel, and
a fourth connector port for placing the chamber in communication with a fourth microchannel.

9. The capping module of claim 8, wherein the substrate includes the first and second connector port formed therein.

10. The capping module of claim 8, wherein:
the first microchannel, the chamber and the second microchannel form a first fluid path, and
the third microchannel, the chamber and the fourth microchannel form a second fluid path.

11. A molecular fractionation device for a microfluidic system, comprising:
a capping module comprising a substrate defining a region for holding a matrix,
a trapping filter for compartmentalizing a matrix on the substrate;
a first connector port for placing the region for holding a matrix in fluid communication with an exterior of the substrate and a first microchannel, wherein the trapping filter covers the connector port, and the first connector port includes a valve for selectively blocking flow through the first connector port, a second connector port for placing the region for holding the matrix in communication with a second microchannel, including a valve for selectively blocking flow through the second connector port, a third connector port for placing the region for holding the matrix in communication with a third microchannel, including a valve for selectively blocking flow through the third connector port, and a fourth connector port for placing the region for holding the matrix in communication with a fourth microchannel, including a valve for selectively blocking flow through the fourth connector port.

12. The molecular fractionation device of claim 11, further comprising a matrix insertion port in communication with the region for holding a matrix for inserting a matrix into the substrate.

13. A microfluidic system, comprising:
a first channel for conveying a sample; and
a plurality of molecular fractionation devices coupled to the channel and arranged in series, such that a first outlet of a first molecular fractionation device is in communication with a first inlet of a second molecular fractionation device, wherein each molecular fractionation device includes a matrix having an affinity for a selected set of molecules, wherein the matrix is disposed in a chamber having a sidewall defined by a trapping filter including a semipermeable membrane.

14. The system of claim 13, further comprising a release channel connected to a second outlet of one of said molecular fractionation devices.

15. The system of claim 13, wherein each molecular fractionation device further includes two outlets, wherein the system further comprises a plurality of release channels, each release channel being connected to a second outlet of one of the molecular fractionation devices.

16. The system of claim 15, wherein each molecular fractionation device further includes two inlets for providing a buffer solution to the matrix.

17. The system of claim 16, further comprising a filtration system coupled to one of said release channels.

18. The system of claim 17, wherein the filtration system comprising a capping module having a membrane for performing a filtering a sample, wherein the capping module is adapted to be stacked on the substrate and placed in communication with the release channel.

19. The system of claim 17, further comprising a capillary electrophoresis column coupled to the filtration system.

20. The system of claim 13, further comprising an ejection component for ejecting a sample fraction from the system.

21. A molecular fractionation device, comprising
capping module having a chamber for holding a matrix having an affinity for selected molecules, a trapping filter including a semipermeable membrane for compartmentalizing the matrix in the chamber, a first connector port for placing the chamber in communication with a first microchannel, a second connector port for placing the chamber in communication with a second microchannel, a third connector port for placing the chamber in communication with a third microchannel, a fourth connector port for placing the chamber in communication with a fourth microchannel, and at least one valve for selectively blocking fluid flow through one of said connector ports.

22. The molecular fractionation device of claim 21, further comprising a sealable matrix insertion port formed in the chamber for inserting the matrix into the chamber.

* * * * *